United States Patent
Brauer et al.

(10) Patent No.: US 10,395,358 B2
(45) Date of Patent: Aug. 27, 2019

(54) HIGH SENSITIVITY REPEATER DEFECT DETECTION

(71) Applicant: KLA-Tencor Corporation, Milpitas, CA (US)

(72) Inventors: Bjorn Brauer, Beaverton, OR (US); Eugene Shifrin, Sunnyvale, CA (US); Ashok Mathew, Fremont, CA (US); Chetana Bhaskar, San Jose, CA (US); Lisheng Gao, Saratoga, CA (US); Santosh Bhattacharyya, San Jose, CA (US); Hucheng Lee, Cupertino, CA (US); Benjamin Murray, Portland, OR (US)

(73) Assignee: KLA-Tencor Corp., Milpitas, CA (US)

( * ) Notice: Subject to any disclaimer, the term of this patent is extended or adjusted under 35 U.S.C. 154(b) by 43 days.

(21) Appl. No.: 15/804,980

(22) Filed: Nov. 6, 2017

(65) Prior Publication Data

US 2018/0130199 A1 May 10, 2018

Related U.S. Application Data

(60) Provisional application No. 62/455,948, filed on Feb. 7, 2017, provisional application No. 62/443,810, filed (Continued)

(51) Int. Cl.
*G06T 7/00* (2017.01)
*G01N 21/95* (2006.01)

(52) U.S. Cl.
CPC ....... *G06T 7/0006* (2013.01); *G01N 21/9501* (2013.01); *G06T 7/001* (2013.01); (Continued)

(58) Field of Classification Search
CPC ..... G06T 7/0006; G06T 7/0004; G06T 7/001; G01N 21/9501
See application file for complete search history.

(56) References Cited

U.S. PATENT DOCUMENTS 7,676,077 B2 3/2010 Kulkarni et al.
7,689,966 B2 3/2010 Verma et al.
(Continued)

OTHER PUBLICATIONS

Chen, Inspection Flow of Yield Impacting Systematic Defects, 2013, IEEE e-Manufacturing & Design Collaboration Symposium, pp. 1-3 (Year: 2013).*

(Continued)

*Primary Examiner* — David F Dunphy
(74) *Attorney, Agent, or Firm* — Ann Marie Mewherter

(57) ABSTRACT

Systems and methods for detecting defects on a reticle are provided. One system includes computer subsystem(s) that include one or more image processing components that acquire images generated by an inspection subsystem for a wafer, a main user interface component that provides information generated for the wafer and the reticle to a user and receives instructions from the user, and an interface component that provides an interface between the one or more image processing components and the main user interface. Unlike currently used systems, the one or more image processing components are configured for performing repeater defect detection by applying a repeater defect detection algorithm to the images acquired by the one or more image processing components, and the repeater defect detection algorithm is configured to detect defects on the wafer using a hot threshold and to identify the defects that are repeater defects.

35 Claims, 8 Drawing Sheets

Related U.S. Application Data on Jan. 9, 2017, provisional application No. 62/242,409, filed on Nov. 10, 2016.

(52) U.S. Cl.
CPC .. *G06T 7/0004* (2013.01); *G06T 2207/10061* (2013.01); *G06T 2207/10152* (2013.01); *G06T 2207/20076* (2013.01); *G06T 2207/20224* (2013.01); *G06T 2207/30148* (2013.01)

(56) References Cited

U.S. PATENT DOCUMENTS

| | | | |
|---|---|---|---|
| 8,041,103 B2 | 10/2011 | Kulkarni et al. | |
| 8,126,255 B2 | 2/2012 | Bhaskar et al. | |
| 8,139,843 B2 | 3/2012 | Kulkarni et al. | |
| 8,664,594 B1 | 4/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 9,134,254 B2 | 9/2015 | Ramachandran | |
| 9,222,895 B2 | 12/2015 | Duffy et al. | |
| 2007/0156379 A1* | 7/2007 | Kulkarni | G06F 17/5045 703/14 |
| 2008/0100844 A1 | 5/2008 | Sali et al. | |
| 2010/0021041 A1 | 1/2010 | Matsui et al. | |
| 2011/0279799 A1* | 11/2011 | Singer | G03F 1/86 355/53 |
| 2011/0320149 A1* | 12/2011 | Lee | G01N 21/9501 702/83 |
| 2013/0322737 A1 | 12/2013 | Murakami et al. | |
| 2014/0195992 A1 | 7/2014 | Ramachandran | |
| 2014/0376801 A1* | 12/2014 | Karsenti | G06T 7/001 382/145 |
| 2015/0221076 A1* | 8/2015 | Gao | G06T 7/001 382/149 |
| 2016/0061745 A1 | 3/2016 | Chen et al. | |
| 2016/0188784 A1 | 6/2016 | Bhattacharyya et al. | |
| 2017/0148226 A1 | 5/2017 | Zhang et al. | |
| 2017/0193680 A1 | 7/2017 | Zhang et al. | |
| 2017/0194126 A1 | 7/2017 | Bhaskar et al. | |
| 2017/0200260 A1 | 7/2017 | Bhaskar et al. | |
| 2017/0200265 A1 | 7/2017 | Bhaskar et al. | |

OTHER PUBLICATIONS

International Search Report for PCT/US2017/060589 dated Feb. 8, 2018.

U.S. Appl. No. 15/603,249, filed May 23, 2017 by Zhang et al. (submitted as U.S. Pat. No. 2017/0345140 published Nov. 30, 2017).

U.S. Appl. No. 15/694,719, filed Sep. 1, 2017 by Zhang et al. (submitted as U.S. Pat. No. 2018/0107928 published Apr. 19, 2018).

U.S. Appl. No. 15/697,426, filed Sep. 6, 2017 by He et al.

* cited by examiner

HIGH SENSITIVITY REPEATER DEFECT DETECTION

BACKGROUND OF THE INVENTION

1. Field of the Invention

The present invention generally relates to systems and methods for high sensitivity repeater defect detection.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

Some current inspection methods detect repeater defects on wafers to thereby detect defects on reticles. For example, if a defect is detected repeatedly ("a repeater defect") at multiple locations on a wafer corresponding to the same location on a reticle, the defects may be caused by the reticle itself. Therefore, repeater defects may be analyzed to determine if they are caused by reticle defects, rather than some other cause.

In general, repeater defect detection (RDD) is performed as a wafer post-processing (PP) operation. For example, the inspection tool may perform normal die-to-die defect detection (DD), and after all wafer defects are reported, the RDD may be performed in a user interface in a post-processing step rather than in a different computer component of the inspection tool. The repeater defects are defined as defects positioned at the same location (within a certain tolerance) in several dies.

There are, however, several disadvantages to the currently used methods and systems for RDD. For example, in order to find weak repeater defects, a substantially hot defect detection needs to be performed. A majority of the detected events are not repeaters and are filtered by RDD. The problem is the tool has a limited capacity for defects stored in the lot result due to band-width (of the internal network of the inspection tool) and disk space. Location is a substantially strong filter that eliminates a majority of the events in the lot results, but for the weak repeaters, the inspection cannot be run hot enough to save all of the candidate defects.

Accordingly, it would be advantageous to develop systems and methods for detecting repeater defects on a wafer that do not have one or more of the disadvantages described above.

SUMMARY OF THE INVENTION

The following description of various embodiments is not to be construed in any way as limiting the subject matter of the appended claims.

One embodiment relates to a system configured to detect defects on a reticle. The system includes an inspection subsystem configured to scan a wafer to thereby generate images for the wafer. A reticle is used to print features on the wafer in a lithography process. The system also includes one or more computer subsystems that include one or more image processing components configured for acquiring the images generated by the inspection subsystem for the wafer. The one or more computer subsystems also include a main interface component configured for providing information generated for the wafer :30 and the reticle to a user and for receiving instructions from the user. In addition, the computer subsystem(s) include an interface component, configured for providing an interface between the one or more image processing components and the main user interface component and for controlling one or more hardware elements of the inspection subsystem. The one or more image processing components are configured for performing repeater defect detection by applying a repeater defect detection algorithm to the images acquired by the one or more image processing components. The repeater defect detection algorithm is configured to detect defects on the wafer using a hot threshold and to identify the defects that are repeater defects. In addition, the one or more image processing components are configured for sending inspection results including information for only the repeater defects to the interface component. The computer subsystem(s) are configured for identifying defects on the reticle based on the repeater defects detected on the wafer. The system may be further configured as described herein.

Another embodiment relates to a computer-implemented method for detecting defects on a reticle. The method includes acquiring images generated for a wafer by an inspection subsystem. A reticle is used to print features on the wafer in a lithography process. The acquiring is performed by one or more image processing components included in one or more computer subsystems. The one or more computer subsystems include a main user interface configured for providing information generated for the wafer and the reticle to a user and for receiving instructions from the user. The one or more computer subsystems also include an interface component configured for providing an interface between the one or more image processing components and the main user interface component and for controlling one or more hardware elements of the inspection subsystem. The method also includes performing repeater defect detection by applying a repeater defect detection algorithm to the images acquired by the one or more image processing components. The repeater defect detection algorithm is configured to detect defects on the wafer using a hot threshold and to identify the defects that are repeater defects. The repeater defect detection is performed by the one or more image processing components. The method further includes sending inspection results including information for only the repeater defects from the one or more image processing components to the interface component. In addition, the method includes identifying defects on the reticle based on the repeater defects detected on the wafer. Identifying the defects on the reticle is performed by the one or more computer subsystems.

Each of the steps of the method may be further performed as described herein. In addition, the method may include any other step(s) of any other method(s) described herein. Furthermore, the method may be performed by any of the systems described herein.

Another embodiment relates to a non-transitory computer-readable medium storing program instructions executable on a computer system for performing a computer-implemented method for detecting defects on a reticle. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
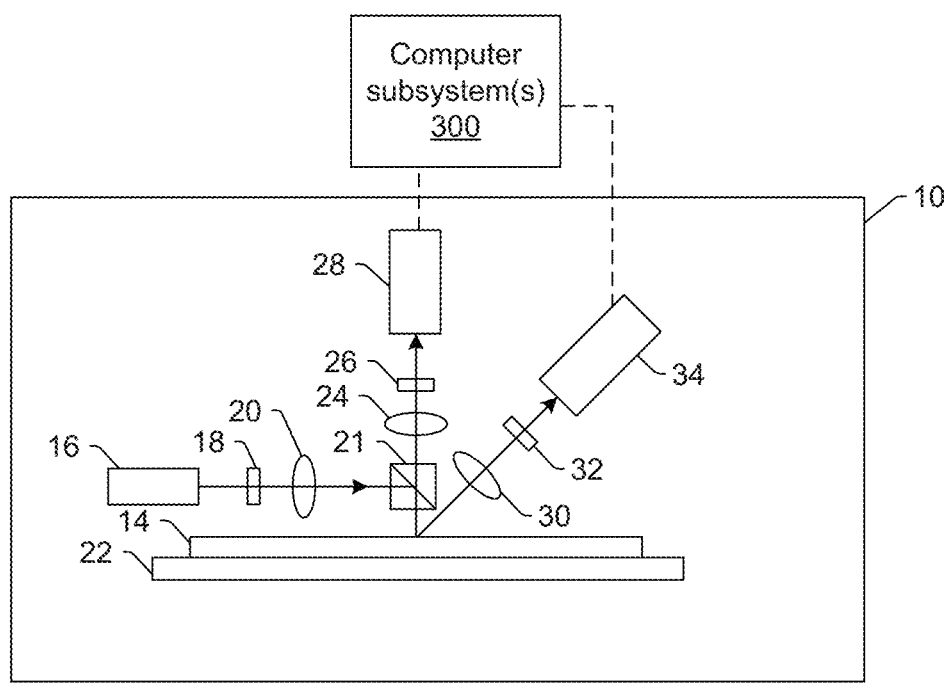
FIGS. 1 and 2 are schematic diagrams illustrating side views of embodiments of a system configured as described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to detect defects on a reticle. The embodiments described herein improve the sensitivity of repeater defect detection (RDD) algorithm(s). There are several ways to approach sensitivity improvements for RDD. They are all based on the common principle that we need to be able to find and save a relatively high number of defect candidates first and apply a die coordinates filter after that. All defect candidates cannot currently be reported in a temporary lot result due to bandwidth limitations, so, in the embodiments described herein, the temporary storage of all defect candidates is moved closer to the defect detection hardware (HW), namely in the one or more image processing components of the inspection tool. It is also substantially likely that a standard defect detection algorithm (e.g., multiple die automatic threshold (MDAT), which is available on some inspection tools commercially available from KLA-Tencor, Milpitas, Calif.) cannot be set hot enough, so a different defect detection algorithm (e.g., nanoMDAT or Fixed Threshold, which are also available on some commercially available inspection tools from KLA-Tencor) may be used to provide a substantially high density of defects. As discussed further below, these changes to the currently used methods and systems provide a number of advantages over the previously used systems and methods for repeater defect detection.

In general, defect detection tools essentially perform data processing in a hierarchical manner: a detection algorithm (in an image computer) sees every pixel of every image of a wafer generated by a detector of an inspection system; a post-processing algorithm (in an image computer) sees only pixels marked as defective; defect classification software (SW) sees only defects, not pixels; and a user interface deals with a significantly reduced data set. Therefore, any detection process step can be described as a filter that sequentially reduces the amount of information content provided to the next detection process step. In each step, noise/irrelevant information is removed and only useful information is kept.

Currently, repeater detection is performed as the very last step of this data reduction process and is performed by the highest level layer, i.e., the main user interface. This works well for strong defects (i.e., defects that produce a strong defect signal) since there is no problem finding the repeater candidate defects in the first place. As weaker and weaker defects/repeaters are to be detected, a problem arises: RDD is a very strong filter by itself. Therefore, it does not make sense to keep the strongest available filter for the last processing stage. One would rather start with it. In addition to this "philosophical" problem, there is another very practical one—the high level layers of the system are designed to handle only a limited amount of data. If you want to find weak repeater defects, you need to run weak defects through the RDD process. "Weak defects" as that term is used herein is generally defined as defects that have relatively weak defect signals or data (e.g., signals or data that are undetectable using a normal threshold, are only detectable using a hot threshold, and may, even with a hot threshold, be marginally detectable with signals or data substantially near (only slightly above) the threshold used for defect detection). The number of weak defects on the wafer is however huge (the sensitivity of the inspection tool is being pushed to the absolute limits). The main user interface and intermediate layers are not capable of handling data of this size. Accordingly, the embodiments described herein aim to move RDD to the image processing components—the lower/lowest level layers of the inspection tool computing.

One embodiment of such a system is shown in FIG. 1. The system includes an inspection subsystem configured to scan a wafer to thereby generate images for the wafer. In general, the inspection subsystems described herein include at least an energy source and a detector. The energy source is configured to generate energy that is directed to a wafer. The detector is configured to detect energy from the wafer and to generate output (e g., images) responsive to the detected energy.

In one embodiment, the energy directed to the wafer includes light, and the energy detected from the wafer includes light. For example, in the embodiment of the system shown in FIG. 1, inspection subsystem 10 includes an illumination subsystem configured to direct light to specimen 14, The illumination subsystem includes at least one light source. For example, as shown in FIG. 1, the illumination subsystem includes light source 16. In one embodiment, the illumination subsystem is configured to direct the light to the wafer at one or more angles of incidence, which may include one or more oblique angles and/or one or more normal angles. For example, as shown in FIG. 1, light from light source 16 is directed through optical element 18 and then lens 20 to beam splitter 21, which directs the light to wafer 14 at a normal angle of incidence. The angle of incidence may include any suitable angle of incidence, which may vary depending on, for instance, characteristics of the wafer and the defects to be detected on the wafer.

The illumination subsystem may be configured to direct the light to the wafer at different angles of incidence at different times. For example, the inspection subsystem may be configured to alter one or more characteristics of one or more elements of the illumination subsystem such that the light can be directed to the wafer at an angle of incidence that is different than that shown in FIG. 1. In one such example, the inspection subsystem may be configured to move light source 16, optical element 18, and lens 20 such that the light is directed to the wafer at a different angle of incidence.

In some instances, the inspection subsystem may be configured to direct light to the wafer at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the wafer at the same time as the other light, one or more characteristics (e.g., wavelength, polarization, etc.) of the light directed to the wafer at different angles of incidence may be different such that light resulting from illumination of the wafer at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the wafer. Multiple illumination channels may be configured to direct light to the wafer at the same time or at different times (e.g., when different illumination channels are used to sequentially illuminate the wafer). In another instance, the same illumination channel may be configured to direct light to the wafer with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the wafer at different times. The illumination subsystem may have any other suitable configuration known in the art for directing the light having different or the same characteristics to the wafer at different or the same angles of incidence sequentially or simultaneously.

In one embodiment, light source 16 may include a broadband plasma (BBP) light source. In this manner, the light generated by the light source and directed to the wafer may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the wafer. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for inspection.

The inspection subsystem may also include a scanning subsystem configured to cause the light to be scanned over the wafer. For example, the inspection subsystem may include stage 22 on which wafer 14 is disposed during inspection. The scanning subsystem may include any suitable mechanical and/or robotic assembly (that includes stage 22) that can be configured to move the wafer such that the light can be scanned over the wafer. In addition, or alternatively, the inspection subsystem may be configured such that one or more optical elements of the inspection subsystem perform some scanning of the light over the wafer. The light may be scanned over the wafer in any suitable fashion.

The inspection subsystem further includes one or more detection channels. At least one of the one or more detection channels includes a detector configured to detect light from the wafer due to illumination of the specimen by the inspection subsystem and to generate output responsive to the detected light. For example, the inspection subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the specimen. However, two or more of the detection channels may be configured to detect the same type of light from the wafer (e.g., specularly reflected light). Although FIG. 1 shows an embodiment of the inspection subsystem that includes two detection channels, the inspection subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the inspection subsystem may be signals or data, but not image signals or image data. In such instances, a computer subsystem such as an image processing component (not shown in FIG. 1) described further herein of the system may be configured to generate images of the wafer from the non-imaging output of the detectors. However, in other instances, the detectors may be configured as imaging detectors that are configured to generate image signals or image data. Therefore, the system may be configured to generate the images described herein in a number of ways.

It is noted that FIG. 1 is provided herein to generally illustrate a configuration of an inspection subsystem that may be included in the system embodiments described herein. Obviously, the inspection subsystem configuration described herein may be altered to optimize the performance of the system as is normally performed when designing a commercial inspection system. In addition, the systems described herein may be implemented using an existing inspection system (e.g., by adding functionality described herein to an existing inspection system) such as the 28xx and 29xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

Computer subsystem(s) 300 of the system may be coupled to the detectors of the inspection subsystem in any suitable manner (e.g., via one or more transmission media, which may include "wired" and/or "wireless" transmission media) such that the computer subsystem(s) can receive the output generated by the detectors during scanning of the wafer. Computer subsystem(s) 300 may be configured to perform a number of functions using the output of the detectors as described herein and any other functions described further herein. Computer subsystem(s) 300 may be further configured as described herein.

Computer subsystem(s) 300 (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device, adapted according to the various embodiments described herein. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and SW, either as a standalone or a networked tool.

Various components of the computer subsystem(s) may be coupled to each other such that images, data, information, instructions, etc. can be sent between the various components as described further herein. For example, different components may be coupled to each other by any suitable transmission media, which may include any suitable wired and/or wireless transmission media known in the art. Two or more of such components may also be effectively coupled by a shared computer-readable storage medium (not shown).

Although the inspection subsystem is described above as being an optical or light-based inspection subsystem, the inspection subsystem may be an electron beam-based inspection subsystem. For example, in one embodiment, the energy directed to the wafer includes electrons, and the energy detected from the wafer includes electrons. In this manner, the energy source may be an electron beam source. In one such embodiment shown in FIG. 2, the inspection subsystem includes electron column 122, which is coupled to computer subsystem(s) 300.

Figure 2:
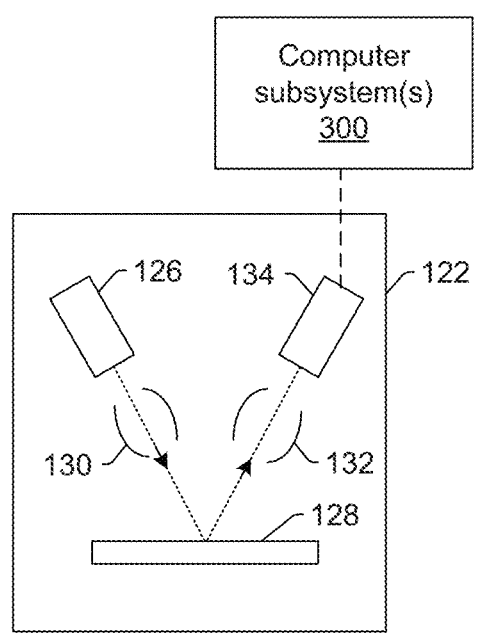

As also shown in FIG. 2, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. Nos. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the wafer at an oblique angle of incidence and are scattered from the wafer at another oblique angle, it is to be understood that the electron beam may be directed to and scattered from the wafer at any suitable angles. In addition, the electron beam-based subsystem may be configured to use multiple modes to generate images of the wafer (e.g., with different illumination angles, collection angles, etc.). The multiple modes of the electron beam-based subsystem may be different in any image generation parameters of the subsystem.

Computer subsystem(s) 300 may be coupled to detector 134 as described above. The detector may detect electrons returned from the surface of the wafer thereby forming electron beam images of the wafer. The electron beam images may include any suitable electron beam images. Computer subsystem(s) 300 may be configured to perform any of the functions described herein using the output of the detector and/or the electron beam images. Computer subsystem(s) 300 may be configured to perform any additional step(s) described herein. A system that includes the inspection subsystem shown in FIG. 2 may be further configured as described herein.

It is noted that FIG. 2 is provided herein to generally illustrate a configuration of an electron beam-based inspection subsystem that may be included in the embodiments described herein. As with the optical inspection subsystem described above, the electron beam-based inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system). For some such systems, the methods described herein may be provided as optional functionality of the system (e.g., in addition to other functionality of the system). Alternatively, the system described herein may be designed "from scratch" to provide a completely new system.

Although the inspection subsystem is described above as being a light- or electron beam-based inspection subsystem, the inspection subsystem may be an ion beam-based inspection subsystem. Such an inspection subsystem may be configured as shown in FIG. 2 except that the electron beam source may be replaced with any suitable ion beam source known in the art. In addition, the inspection subsystem may be any other suitable ion beam-based subsystem such as those included in commercially available focused ion beam (FIB) systems, helium ion microscopy (HIM) systems, and secondary ion mass spectroscopy (SIMS) systems.

As noted above, the inspection subsystem is configured for scanning energy (e.g., light or electrons) over a physical version of the wafer thereby generating actual images for the physical version of the wafer. In this manner, the inspection subsystem may be configured as an "actual" tool, rather than a "virtual" tool. For example, a storage medium (not shown) and computer subsystem(s) (not shown) may be configured as a "virtual" tool. In particular, the storage medium and the computer subsystem(s) of a virtual tool are not part of inspection subsystem 10 and do not have any capability for handling the physical version of the wafer. In other words, in tools configured as virtual tools, the output of its one or more "detectors" may be output that was previously generated by one or more detectors of an actual tool and that is stored in the virtual tool, and during the "scanning," the virtual tool may replay the stored output as though the wafer is being scanned. In this manner, scanning the wafer with a virtual tool may appear to be the same as though a physical wafer is being scanned with an actual tool, while, in reality, the "scanning" involves simply replaying output for the wafer in the same manner as the wafer may be scanned, Systems and methods configured as "virtual" inspection tools are described in commonly assigned U.S. Pat. Nos. 8,126,255 issued on Feb. 28, 2012 to Bhaskar et al. and U.S. Pat. No. 9,222,895 issued on Dec. 29, 2015 to Duffy et al., both of which are incorporated by reference as if fully set forth herein. The embodiments described herein may be further configured as described in these patents. For example, the one or more computer subsystems described herein may include a virtual inspector configured as described in these patents. In addition, configuring the one or more virtual systems as a central compute and storage (CCS) system may be performed as described in the above-referenced patent to Duffy. The persistent storage mechanisms described herein can have distributed computing and storage such as the CCS architecture, but the embodiments described herein are not limited to that architecture.

As further noted above, the inspection subsystem may be configured to generate output for the wafer with multiple modes. In general, a "mode" can be defined by the values of parameters of the inspection subsystem used for generating output for a wafer. Therefore, modes that are different may be different in the values for at least one of the imaging parameters of the inspection subsystem. For example, in one embodiment of an optical based inspection subsystem, at least one of the multiple modes uses at least one wavelength of light for illumination that is different from at least one wavelength of the light for illumination used for at least one other of the multiple modes. The modes may be different in the illumination wavelength as described further herein (e.g., by using different light sources, different spectral filters, etc.) for different modes. In another embodiment, at least one of the multiple modes uses an illumination channel of the inspection subsystem that is different, from an illumination channel of the inspection subsystem used for at least one other of the multiple modes. For example, as noted above, the inspection subsystem may include more than one illumination channel. As such, different illumination channels may be used for different modes.

A reticle is used to print features on the wafer in a lithography process. The lithography process may include any suitable lithography process. In general, a lithography process uses some form of energy (e.g., light, electrons, etc.) to transfer a pattern formed on a reticle to a material on a wafer. The material on the wafer may be some form of resist, one or more properties of which change after exposure to the energy used in the lithography process. In this manner, a pattern of energy (light, electrons, etc.) can be directed from or through a reticle to a resist on a wafer to thereby transfer the pattern from the reticle to the resist. One or more additional steps may be performed on the resist (e.g., post exposure bake, development, etc.) to complete the pattern transfer process. Therefore, as can be clearly seen from this general description of lithography processes, defects that are present on a reticle can be transferred to a wafer in the lithography process, which is obviously disadvantageous. As further described herein, sometimes it is not possible to inspect a reticle directly, as in a reticle inspection process. In such instances, the reticle is printed on a wafer, the wafer is inspected for defects, and those wafer defects are used to determine if the defects are caused by the reticle. Such determinations may be performed as described further herein.

Figure 3:
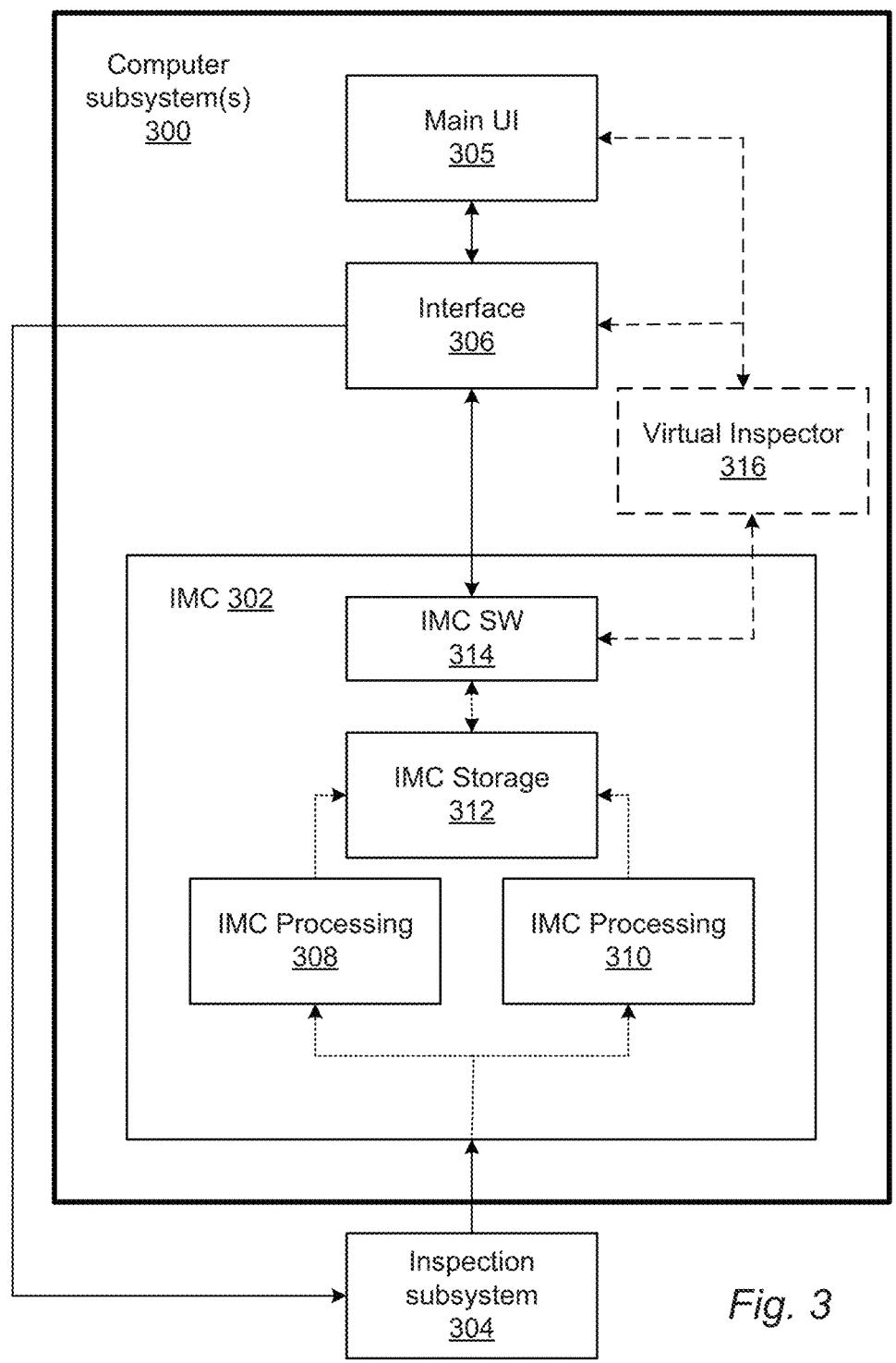
FIG. 3 is a block diagram illustrating one embodiment of one or more computer subsystems that may be included in the system embodiments described herein.

The one or more computer subsystems include one or more image processing components configured for acquiring the images generated by the inspection subsystem for the wafer. The one or more image processing components are also generally and collectively referred to herein as the "IMC" for the sake of brevity. As such, when the term "IMC" is used herein, it is meant to be defined as any of the embodiments of the one or more image processing components described herein. In one such embodiment shown in FIG. 3, computer subsystem(s) 300 include IMC 302. Acquiring the images may be performed using one of the inspection subsystems described herein (e.g., by directing light or an electron beam to the wafer and detecting light or an electron beam, respectively, from the wafer). For example, as shown in FIG. 3, inspection subsystem 304 may be coupled to IMC 302 such that images generated by the inspection subsystem can be sent to IMC 302 and/or acquired from the inspection subsystem by IMC 302. In this manner, acquiring the images may be performed using the physical wafer itself and some sort of imaging HW. Inspection subsystem 304 may be configured according to any of the embodiments described herein.

As further shown in FIG. 3, IMC 302 may include a number of components including IMC processing components 308 and 310, IMC storage 312, and IMC SW 314. IMC processing components 308 and 310 may have the same configuration as each other and may operate in parallel. For example, during scanning performed by inspection subsystem 304, some of the images generated by the inspection subsystem may be acquired by IMC processing component 308 and others of the images generated by the inspection subsystem may be acquired by IMC processing component 310. In general, a SW component such as IMC SW 314 may control which of the images get sent to (and therefore acquired by) the different IMC processing components. The IMC processing components may then perform the same processes on the images that they acquired simultaneously. IMC processing components 308 and 310 may therefore be configured as parallel processing components. In addition, the IMC may be configured as a cluster of servers that acquires wafer data from the detectors of the inspection subsystem and schedules parallel processing of image processing algorithms. Although two IMC processing components are shown in FIG. 3, it is to be understood that the IMC may include as many or as few IMC processing components as desired. IMC processing components 308 and 310 may be further configured as described herein.

IMC storage 312 may be generally referred to herein as a shared memory and may be configured as a shared non-transitory computer-readable storage medium that is accessible for multiple processes performed by the one or more image processing components. For example, defect detection in IMC may be implemented as parallel processing in which multiple central processing units (CPUs) are working in parallel on the input data stream. Every SW process may have its own memory space. This makes the system more robust, but creates problems for data transfer between the different processes. Shared memory is a memory in the IMC that is made available to all processes. This non-transitory computer-readable storage medium may be further configured as described herein. In some instances, IMC storage 312 may be configured as shown in FIG. 3 so that IMC processing components 308 and 310 send results to the IMC storage. However, IMC storage 312 may also or alternatively be configured to receive or acquire images from the inspection subsystem and to send those images to the various IMC processing components as necessary, requested, or instructed, IMC storage 312 may also include a variety of different types of memory having a variety of different characteristics (e.g., sizes) as described further herein depending on the configuration of the various embodiments described herein.

IMC SW 314 may be configured for receiving instructions from other components included in the one or more computer subsystems as described further herein and for controlling or instructing the IMC processing components 308 and 310 and/or IMC storage 312 so that these components perform various steps or functions described further herein. In this manner, the IMC SW may run the IMC itself and the image processing algorithms performed by the IMC. IMC SW may have various configurations depending on the steps or functions described herein.

The computer subsystem(s) also include a main user interface component configured for providing information generated for the wafer and the reticle to a user and for receiving instructions from the user. The main user interface component is also referred to herein as simply the "Main UI" for the sake of brevity. In one such embodiment, as shown in FIG. 3, computer subsystem(s) include Main UI 305. The Main UI may have a variety of different configurations depending on the functions and/or steps to be performed by the Main UI and the systems described herein. In general, however, the Main UI may include one or more display components (not shown) configured for displaying information to a user, for prompting a user for input, for providing a user with a means for entering input, etc. and one or more processing elements (not shown) configured for performing one or more functions or steps such as those described further herein as being performed by a Main UI and/or requested to be performed by a user. The Main UI may be implemented using any HW, SW, code, etc., that can be adapted to perform the function(s) of the Main UI described herein.

The computer subsystem(s) further include an interface component configured for providing an interface between the one or more image processing components and the main user interface component and for controlling one or more HW elements of the inspection subsystem. For example, as shown in FIG. 3, computer subsystem(s) 300 include interface 306. The interface component may be configured to send instructions to one or more HW elements (not shown in FIG. 3) of inspection subsystem 304, which may include any of the HW elements of the inspection subsystems shown in FIGS. 1 and 2. The interface component may be coupled to the inspection subsystem as described further herein such that the interface component can control and/or alter one or more parameters of one or more HW elements of the inspection subsystem.

The interface component is also coupled to the IMC as shown in FIG. 3. The interface and the IMC may be coupled as described further herein such that instructions, information, results, images, etc. can be sent between the interface and the IMC. The interface may also be coupled to Main UI 305 as shown in FIG. 3 in a similar manner such that similar information may be sent between the interface and the Main UI. Therefore, interface 306 provides an interface between IMC 302 and Main UI 305. In addition, interface 306 may be the machine control component of the wafer inspector SW and may essentially be configured as a lower tier of the Main UI. Interface 306 may include a variety of HW and/or SW components that can be configured to perform the functions and/or steps of the interface component described further herein. Interface 306 may be further configured as described herein.

The wafer inspector HW/SW may therefore be configured as a multi-layered HW/SW system in which the different tiers include the IMC that is the lowest level and "closest" to the HW of the inspection subsystem, the interface that is the intermediate level and between the IMC and the Main UI, and the Main UI which is the highest level, furthest removed from the inspection subsystem HW and "closest" to the user.

The one or more image processing components are configured for performing repeater defect detection (RDD) by applying an RDD algorithm to the images acquired by the one or more image processing components. Therefore, unlike currently used methods and systems, the embodiments described herein are configured for performing RDD in the IMC. The RDD may be performed in a variety of different ways described further herein. Moving the RDD into the IMC as opposed to how it is currently performed provides significant advantages as described further herein.

The RDD algorithm is configured to detect defects on the wafer using a hot threshold and to identify the defects that are repeater defects. The term "repeaters" is used interchangeably herein with the term "repeater defects." A "hot threshold" can be generally defined as a threshold used for detecting potential defects and defects that is set intentionally at or substantially near the noise floor of the images generated by the scanning. "Hot scans" performed using a hot threshold are typically performed to detect as many potential defects and actual defects as possible to ensure that the most defects or all of the interesting defects are captured and/or to ensure that defects having relatively weak signals are captured. The hot threshold may be applied to the images of the wafer, any signal images or data above the hot threshold may be identified as potential defects, and signals or data that are not above the hot threshold are not identified as potential defects.

In one embodiment, the RDD algorithm is configured to identify the defects that are the repeater defects by comparing the within die defect coordinates for different of the defects to each other. For example, as described further herein, the IMC performs the first step in the data reduction by identifying defects that repeat in some manner. In general, at this step, the RDD algorithm will be detecting defects that are die repeaters even though die repeaters are not of interest for the embodiments described herein. For example, after the die repeaters have been identified by the RDD algorithm, the die repeaters can be analyzed to determine which of the die repeaters are reticle repeaters. In this manner, identifying the defects that are the repeater defects may be performed by the RDD algorithm in the IMC by comparing within die defect coordinates to each other. Defects having the same within die defect coordinates (or "die relative defect coordinates") can then be identified as defects that repeat from die-to-die. Those defects may then be the only defects that are passed on for further repeater analysis.

In some instances, the defects will not be reported in die relative coordinates by the IMC. In other words, when the IMC detects a defect, the coordinates of the location of that defect may not be determined by the IMC with respect to a die in which it was detected. In this manner, the coordinates of the defects determined by the IMC may be translated into die coordinates by the IMC. The coordinates may be translated in a number of different ways some of which are described in detail herein. For example, one relatively straightforward way is to translate the coordinates reported for the defects to a reference that is common to the wafer and the die such as a design for the wafer. In one such example, the images generated for the defects by the inspection subsystem can be aligned to the design for the wafer. Once the design coordinates of the defects are determined, those coordinates can be translated to die coordinates based on the known relationship between the design and the die. The die coordinates determined for each of the defects can then be compared to each other, and defects having substantially the same die coordinates can be identified as die repeaters.

Substantially the same die coordinates may be identified by using some repeater distance threshold that defines how close two die coordinates have to be to be determined as locations of die repeaters. For example, minor errors in the printing of the design on the wafer, the positioning elements of the inspection subsystem, etc. may cause two identical within die locations to have slightly or somewhat different die coordinates determined for them. In this manner, it may be useful to use a tolerance for determining which within die coordinates can be considered to be the same. The specific values of that tolerance can be determined in any of the commonly used ways for determining such a tolerance and based on at least the information described above.

The one or more image processing components are configured for sending inspection results that include information for only the repeater defects to the interface component. For example, the IMC may return die repeaters only. In particular, although the IMC may detect defects that are determined to not be repeaters, because the defects of interest (DOIs) for the system configurations described herein are the repeater defects, information for the detected non-repeater defects can be discarded after they are determined to be non-repeaters. In this manner, the IMC will perform defect detection followed by the first data reduction (or filtering) step in which the defect detection information is filtered for non-repeaters.

The IMC may send the inspection results to the interface component in any suitable manner, which is enabled by the configuration described further herein. In addition, the IMC component may send the information for only the repeater defects in any suitable format to the interface component. The information for only the repeater defects that is included in the inspection results and sent to the interface component may include any information that is generated for the repeater defects by the IMC, which may include, but is not limited to, defect coordinates, patch images, defect attributes, etc. Furthermore, as described further herein, in some embodiments, the computer subsystem(s) include or make use of a split database (DB) in which different information for the defects is stored in different memory mediums. In this manner, the IMC may send only a portion of the inspection results to the interface component while another portion of the inspection results is sent to a different component. Still, both portions of the inspection results will only include results for the repeater defects and will not include results for the non-repeaters.

The one or more computer subsystems are configured for identifying defects on the reticle based on the repeater defects detected on the wafer. For example, further repeater analysis may be performed by the Main UI to suppress die repeaters and keep reticle repeaters. Although the Main UI may be selected as the most advantageous component for performing the identification of the reticle repeaters, other components of the computer subsystem(s) could be configured and used for this step. For example, if the computer subsystem(s) include a virtual inspector (VI), then the VI may be used for identifying the repeater defects. In addition, other components such as the IMC and interface component could be configured to perform such identifying.

For the purpose of the applications described herein, the user wants to keep only reticle repeaters. Repeaters that are both reticle and die repeaters should be removed from the final report. In particular, the embodiments described herein were created for applications in Which the user is looking for the repeater defects that are produced due to problems with the reticle (photomask). Defects that are present at the same location in different dies on the same reticle are, most likely, caused by wafer processing—not by the reticle itself.

In other words, defects that appear on the wafer at substantially the same location in multiple dies of a single reticle are likely not due to actual reticle defects such as a damaged patterned feature, a particle or foreign matter, and the like. Instead, if a defect repeats on a wafer in multiple dies in a reticle, the defects on the wafer that repeat in the dies are likely due to an interaction issue between the reticle, wafer, and process (e.g., a marginal design that is failing due to a design/process interaction issue). While such die repeater defects may be interesting in some use cases, the embodiments described herein have been created specifically for detecting defects that repeat from printed reticle instance to printed reticle instance and can therefore be assumed to be caused by reticle defects.

In one embodiment, the one or more computer subsystems are configured for identifying the defects on the reticle by determining which of the repeater defects repeat in two or more printed instances of the reticle on the wafer and identifying the repeater defects that repeat in the two or more printed instances of the reticle on the wafer as the defects on the reticle. For example, as described further herein, the defects that are of interest for the systems and methods described herein are repeaters that repeat with respect to the reticle and can therefore by reasonably attributed to the reticle itself rather than some other element involved in the printing of the wafers. Therefore, if more than one defect detected on the wafer appears at the same within reticle coordinates (coordinates with respect to the reticle rather than the wafer, the inspection system, etc.), then the defects can be determined to be reticle repeaters that may be caused on the wafer by a defect on the reticle at the within reticle coordinates of the defects.

In some instances, the defects will not be reported in reticle coordinates by the IMC. In other words, when the DAC detects a defect, the coordinates of the location of that defect may not be determined by the IMC with respect to a reticle. In this manner, the coordinates of the defects determined by the IMC may be translated into reticle coordinates by the IMC or more likely by the components (e.g., the Main UI) that identifies the reticle repeater defects. The coordinates may be translated in a number of different ways some of which are described in detail herein. For example, one relatively straightforward way is to translate the coordinates reported for the defects to a reference that is common to the wafer and the reticle such as a design for the wafer and the reticle. In one such example, the images generated for the defects by the inspection subsystem can be aligned to the design for the wafer. Once the design coordinates of the defects are determined, those coordinates can be translated to reticle coordinates based on the known relationship between the design and the reticle. The reticle coordinates determined for each of the defects can then be compared to each other, and defects having substantially the same reticle coordinates can be identified as reticle repeaters.

Substantially the same reticle coordinates may be identified by using some repeater distance threshold that defines how close two reticle coordinates have to be to be determined as locations of reticle repeaters. For example, minor errors in the printing of the design on the wafer, the positioning elements of the inspection subsystem, etc. may cause two identical within reticle locations to have slightly or somewhat different reticle coordinates determined for them. In this manner, it may be useful to use a tolerance for determining which reticle coordinates can be considered to be the same. The specific values of that tolerance can be determined in any of the commonly used ways for determining such a tolerance and based on at least the information described above.

In some embodiments, the one or more image processing components are configured for storing information for all of the detected defects. In this manner, unlike currently used systems and methods, the embodiments described herein may be configured for saving all defects in IMC memory until the end of wafer inspection. The information for all of the detected defects may include any of the information generated for the detected defects by the IMC. The information for all of the detected defects may be stored in any suitable manner. In addition, as described further herein, the embodiments may be configured to store all of the information for the detected defects in a variety of different ways, e.g., using a split DB included in the IMC.

The IMC preferably stores the information for all of the detected defects such that the information for all of the detected defects is available for RDD. Once RDD is performed by the IMC, the information that was stored for defects determined to not be repeaters may be eliminated from the stored information prior to sending that information to one or more other components of the computer subsystem(s)

In a further embodiment, performing the RDD is performed for only a single swath on the wafer. In this manner, the embodiments described herein may be configured for job-level RDD. In this embodiment, RDD may be performed on the single swath level in the detection code itself. Such RDD allows extremely high density of the preliminary defect candidates, but defects that do not repeat in a die row on the wafer are going to be missed.

In job-level RDD, frame-to-frame alignment is substantially precise and accurate inside one job, so it is possible to do repeater detection as post-processing (PP) on the IMC with substantially tight tolerances (e.g., smaller than a pixel). In order to get the maximum benefit from frame-to-frame alignment, the job size may be increased from the current 12 frames maximum to a full die row (i.e., all dies in a single row on the wafer and/or multiple swaths). However, there is no need to use all dies for feature image (median) computation. Instead, for such computations, 12 frames should be sufficient. Any throughput reduction due to work balancing should not be substantial. IMC will return die repeaters only and further repeater analysis may be performed by the Main UI to suppress die repeaters and keep reticle repeaters.

The advantages of this solution are low implementation effort (IMC code only), no additional HW requirements, and relatively high throughput. Therefore, this embodiment may be implemented relatively cheaply and quickly. One potential disadvantage of this solution is that it may not detect substantially soil repeaters (e.g., if repeaters are so soft that they do not repeat in a die row, this solution will miss them all). Other embodiments described herein may be more suitable for detection of relatively small weak repeater defects.

In another embodiment, the one or more image processing components are configured as a virtual inspector, and the one or more computer subsystems are configured for disconnecting the virtual inspector from the inspection subsystem after the images are acquired from the inspection subsystem and before the RDD is performed. In this manner, the embodiments described herein may be configured for patch-based virtual inspector (VI) approaches. In these embodiments, all defect data and defect patches may be stored on the VI, and a new application running on the VI only (inspection tool is free to run the next inspection) is used for RDD. Detected repeater defects may be reported as a new lot result on the VI.

As described above, patch-based VI approaches involve saving all defect candidates on the patch-based VI. The planned VI capacity may be relatively high (e.g., 150 defects per frame). In addition, the capacity is limited by the disk space, not the data transfer rate (at least in currently used VI configurations, the data is being recorded in real time). There is also no need to keep the defect candidates for any significant amount of time (e.g., record candidates from one inspection, process them, and remove the data). Therefore, most likely, it should be possible to run even hotter inspections. With relatively high defect density, it may be preferable to save the whole wafer image on the VI and, as described further herein, keep defect coordinates in a parallel DB. RDD requires defect coordinates only, and defect patches can be extracted later for repeaters only.

Implementation-wise, the above described embodiments are reasonably straight forward: running hot inspections, saving all defect candidates on the VI, disconnecting the inspection tool from the VI so the inspection tool is available for the next inspection, on the VI initiating a new inspection type for RDD, finding repeaters using defect coordinates (they are saved as part of patch records), and returning defect locations, attributes, and patches (everything already calculated and pre-saved on the VI) to the Main UI. Another advantage of the above described embodiments is that tool throughput is relatively high and development efforts are substantially reasonable. In some cases, the embodiments can increase the cost of ownership (CoO) if the system does not already include a VI.

In an additional embodiment, the one or more image processing components are configured for performing single swath-multiple die row defect detection by applying a defect detection algorithm to the images generated by the inspection subsystem for the same single swath in multiple die rows on the wafer and for sending results of the single swath-multiple die row defect detection to the interface component, and the interface component or the main user interface component performs RDD on the results of the single swath-multiple die row defect detection. In this manner, the embodiments described herein may be configured for a special swath layout approach. For example, instead of swathing the whole wafer sequentially, the inspection subsystem can scan one swath in every die row, then the inspection subsystem can return to the first die row to scan the next swath and so forth.

In this manner, this embodiment may reduce the number of defects saved by the computer subsystem(s) by changing the swathing sequence: instead of swathing every die row sequentially, every first swath for every die row may be scanned and all defects may be reported, then every second swath for every die row and so forth. For example, repeater defects by definition happen in the same location in every die or reticle depending on the type of repeater defects. Therefore, to perform RDD, we do not need the defects from the whole wafer. Instead, it is sufficient to have all defects from some portion of it (e.g., every first swath of every die row, every second swath of every die row, and so forth). The computer subsystem(s) can perform RDD for these defects, report them, and then proceed with other areas. In addition, multiple swaths in every die row may be scanned before proceeding to the next die row when the images generated for the multiple swaths can be processed simultaneously in parallel.

All defect candidates may either be saved in a temporary buffer in the interface component or reported to the Main UI. After every iteration, the interface component or the Main UI may perform RDD and report and/or keep repeater defects only. For example, the interface component may receive results of the scanning in a normal fashion, perform inter-job, inter-sub-swath merging and prior to sending defects to the Main UI, run RDD with zero pixel coordinate tolerance (i.e., pixel to design alignment is working). For example, the IMC may perform defect detection using certain chunks of data (images) called jobs. In order to perform defect detection without gaps, we need some overlap between the images, seen by the neighboring jobs. As a result, some defects may be reported twice from the IMC. Such reported defects should be merged into a single defect by the higher level SW (e.g., the interface component). There is also a recipe parameter called "merge distance" in which two visibly different defects that are less than a merge distance apart should be reported as a single defect. This merging process may be performed in the IMC (intra-job merging) and by the interface component between the jobs and sub-swaths (inter-job/sub-swath) merging.

Alternatively, all defects may be reported to the Main UI that will run RDD prior to saving defects to the disk. The interface-based solution is preferable since it reduces the network load. Of course, the interface component will need additional memory to keep all of these defects, but this requirement is not too high. For a typical wafer, there are maybe 20 die rows. So defects detected in 20 swaths are to be kept, Advantages of the embodiment described above include moderate memory requirements and relatively localized SW changes. Setting up such a configuration may involve minimal changes in the defect detection code and no changes in the interface component. However, setting up this configuration involves interface component involvement, significant changes in swathing control, defects post processing, and Main UI swath progress update and defect handling. Therefore, this configuration may have a significant development effort cost and no new HW costs. This system configuration may have a reduced throughput (compared to other embodiments described herein) due to additional stage travels in Y and the defect candidate density may still be insufficient due to the limitations of available memory. It is also very likely that run time alignment (RTA) may have serious issues due to the absence of previous swath history. For example, there may be potential RTA problems due to broken (unavailable) RTA history.

While the special swath layout approach is most likely insufficient for real solutions, it may be particularly useful as a fast and simple proxy for testing. For instance, it can be used to run a hot inspection with an extremely small sampling plan and generate about two million defect candidates in the Main UI. After that, RDD can be performed in the Main UI using extremely small repeater tolerance (inspection should be using pixel to design alignment) and determining whether sufficient sensitivity can be achieved in this way.

In this manner, some configurations of the systems and methods described herein may be more useful for one application or another. As such, in some instances, it may be advantageous for the systems and methods described herein to be capable of multiple configurations described herein to therefore provide multiple options for performing RDD depending on the application.

In an embodiment, the one or more image processing components include a shared non-transitory computer-readable storage medium accessible for multiple processes performed by the one or more image processing components, and the RDD algorithm is configured to detect the defects on the entire inspected area of the wafer, to store all of the detected defects in the shared non-transitory computer-readable storage medium, and to identify the defects that are the repeater defects using all of the stored detected defects for the entire inspected area of the wafer. In this manner, the embodiments described herein may be configured for IMC based RDD. For example, a shared memory in IMC can be used to keep all defect candidates (for the whole wafer). After all swaths are finished, special jobs may be run to perform RDD and report repeaters to the higher level SW. Such a configuration may require a significant increase of installed physical memory in the IMC.

In the embodiment described above, therefore, the biggest portion of the RDD is done in the IMC. In this case, the majority of the work is to be done by the IMC although some work on the interface component side may be involved. The Main UI is almost not involved. In particular, the main idea is to accumulate all defect candidates in the IMC memory up to the end of wafer inspection. A normal defect detection may be run. A "no defects" result buffer may be returned to the interface component, and all defect candidates may be saved in the shared memory.

One advantage of this embodiment is that the memory is easily scalable to accommodate any desired number of defect candidates per frame, swath, die row, die, wafer, etc. Different types of memory can be used for storing defect information and other results in this embodiment as well such as solid state drive (SSD) storage (flash memory), dynamic random access memory (DRAM), etc. In addition, it is possible to increase the defect candidate density by an order of magnitude if desired by dropping defect patch images and reducing the size of the data structure kept for defects.

In the embodiment described above, after defect detection is performed and all defect candidates are in the shared memory, the interface component may start a new process or (preferably) submit new jobs (of new job type) to the image processing component(s). The IMC code may perform inter-job defects merge and RDD using the defect candidates that are available. Since the data in the shared memory can be organized by swath-sub-swath number, load balancing can be performed in a very easy way: just assigning swath-sub-swath number to process to CPU core (when the CPU includes multiple cores). The shared memory management and load balancing (e.g., swath to core assignment) may be performed by the interface component as well as new job type queuing and submission. After the RDD is performed, the IMC may be able to return repeater defects in a normal result buffer thereby minimizing the changes on the interface component side.

It is noted that RDD may be based on the die coordinates (with all stage corrections applied). These coordinates are not available in the IMC today. They can be transferred using existing mechanisms. Until now, they have been considered unnecessary for the IMC processes. Making this information available in the algorithm most likely means that the IMC will start returning defect locations in wafer rather than swath coordinates, i.e., significant changes to the tool architecture in general. Eventually, the coordinate reporting system may be changed for all inspection types to avoid confusion. Inter-swath merging may be performed by the interface component as is currently performed, but coordinate translation to the wafer coordinate system may be performed in the IMC.

In general, therefore, the IMC-based embodiment described above may have a significant development effort cost, a moderate HW cost (for memory), and low throughput effect. An advantage of the IMC-based embodiments described above is the substantially high throughput.

In some embodiments, the one or more image processing components are configured for performing single swath-multiple die row defect detection by applying a defect detection algorithm to the images generated by the inspection subsystem for the same single swath in multiple die rows on the wafer and storing results of the single swath-multiple die row defect detection in a shared non-transitory computer-readable storage medium in the one or more image processing components accessible for multiple processes performed by the one or more image processing components, and the RDD algorithm is configured to detect the defects in the entire inspected area of the same single swath in the multiple die rows, to store all of the detected defects in the shared non-transitory computer-readable storage medium, and to identify the defects that are the repeater defects using all of the stored detected defects for the entire inspected area of the same single swath in the multiple die rows. In this manner, the embodiment may combine two ideas described further herein: namely, the special swath layout combined with IMC based RDD.

This approach solves any IMC memory problems, since there is no need to keep all candidates in the shared memory until the end of inspection. RTA problems may still occur and may be serious in some instances. The number of swaths that can be processed collectively may be varied depending on the length of the swaths (e.g., for shorter die rows and therefore shorter swaths, more swaths may be processed together compared to longer die rows) without compromising the number of defects that can be kept. Altering parameters of the inspection depending on the length of the die rows and therefore the swaths can optimize swathing for throughput and reduce the number of Y direction stage motions performed during inspection. In addition, like other embodiments described herein, in this embodiment, the amount and type of memory may be varied depending on the number of defects to be kept for processing.

More defects and swaths can also be kept and processed collectively by not storing defect patches, which may partially solve the broken RTA history problem. For example, in order to perform die-to-die comparisons (defect detection), images need to registered (aligned) from the different dies. This process is called RTA and is performed by dedicated HW/SW. This is a fairly complicated process that utilizes the history of the alignment for the previous swaths. The proposed scanning scheme may therefore make it impossible for RTA to use the history and it may result in alignment quality degradation.

The special swath layout combined with IMC-based RDD is a combination the two approaches described above and allows extreme defect candidate density and possibly the highest sensitivity of the embodiments described herein. The idea is to perform defect candidate detection for every first swath (or every n swaths when sufficient parallel computing is available) for all die rows keeping all defect candidates in the IMC shared memory, performing RDD for these defect candidates, and returning the results to the interface component and Main UI without collecting the data for the rest of the wafer. The throughput reduction will be similar to that in the first approach, but we will be able to use the whole shared memory for this small part of the wafer, which allows increasing defect candidate density proportionally.

In another embodiment, the one or more image processing components include a shared non-transitory computer-readable storage medium accessible for multiple processes performed by the one or more image processing components, the one or more computer subsystems include a virtual inspector, the one or more image processing components are configured for storing only a first portion of results produced by the RDD algorithm in the shared non-transitory computer-readable storage medium and only a second portion of the results produced by the RDD in the virtual inspector, the first portion includes only defect coordinates for the defects detected on the wafer, the second portion includes only defect attributes and patch images for the detected defects on the wafer, the RDD algorithm is configured to identify the repeater defects using only the first portion of the results, and the one or more image processing components are configured for retrieving the defect attributes and patch images for the repeater defects from the virtual inspector and generating the inspection results by combining information generated by identifying the repeater defects with the retrieved defect attributes and patch images. In this manner, the embodiments described herein may be configured for persistent storage (including patch-based VI or local (on the IMC) storage) combined with IMC based RDD.

This approach may utilize a "split" or "distributed" DB. For example, repeater detection is based on die (reticle) defect coordinates only, so we can keep defect coordinates in the shared memory on the IMC and save defect attributes and patch images in some temporary storage (like a VI or a local hard drive (HDD)/SDD, where "local" in this context means that these devices are installed in the IMC and available to SW running on the IMC, although both the VI and the local storage may be HDDs or SSDs). For example, as shown in FIG. 3, computer subsystem(s) 300 may optionally include virtual inspector 316, which may be configured as described further herein.

In other words, the IMC may run a defect detection. Defect coordinates may be saved in the IMC DB. Defect images and attributes are saved in the persistent storage (SSD/HDD/RAID DB, i.e., a DB that resides on some type of persistent storage: hard drive, solid state, etc.). The two DBs may use the same keys. The small and fast DB keeps coordinates only while the big semi-permanent DB keeps defect images and features/attributes. In this manner, to perform RDD, some data (for defects) needs to be saved for further processing. Some portions of this data is used by RDD per se and should be easily accessible (for fast access in order to perform RDD fast enough). Other portions of the defect information are not used by RDD but are to be reported to a user and/or the Main UI. This information can be saved in a different location with significantly slower access speeds (and it can be much bigger in size, since it can be saved on the cheaper storage devices).

After wafer scanning is performed, special jobs may be run for RDD and relevant defect candidate data from the storage may be retrieved. For example, the DRAM-based DB, which includes the defect coordinates, may be used for repeater analysis. The repeater analysis may generate repeater coordinates, Which can be used to extract images and features from the second DB (stored in the persistent storage). The defect coordinates can be combined with the extracted images and features to generate the lot results that include only repeaters. The rest of the defect candidates can be discarded at this point. Estimation shows that without additional physical memory, up to 1900 defect candidates per frame can be kept. Up to 3 TB of storage per node may be needed to keep temporary data. In this manner, the embodiments described herein may be configured for splitting the defect data for RDD and defect attributes calculation/reporting.

The approach described above is based on the fact that RDD requires only defect coordinates—neither patches nor attributes are necessary. As such, the defect structure can be saved for every defect candidate on the VI or the local IMC storage and defect coordinates can be stored in the shared memory. Therefore, the size of the defect structure used for RDD may be reduced to bounding box coordinates (e.g., 4 integers) and die row, swath in a die row, frame number (or something similar) and the whole defect takes only 8 integers in the shared memory buffer. As such, more defects can be stored without increasing the currently used memory capacity. After the RDD is performed, the corresponding patch images and defect attributes can be uploaded from the storage (a substantially small amount of data) and sent to the interface component and Main UI in a standard way (some changes to results buffer, i.e., memory used to transfer results from the IMC to the interface component, may still be made).

In the above described embodiment, therefore, the proposed sequence of operations may be: running a substantially hot full wafer inspection; saving defects on persistent storage and defect coordinates in the shared memory; the interface component issuing jobs of new type—RDD jobs, and IMC finding all repeater defects; reading corresponding defect records from storage; and returning the results to the interface component or Main UI. The storage can be freed immediately after inspection. If desired, the available bandwidth (writing speed) for saving defect candidates to storage can be altered (e.g., by changing the storage type) based on the number of defect candidates to be stored and the desired throughput. The I/O, most likely, can work in parallel with data processing. Advantages of these embodiments include that they should provide substantially high sensitivity for RDD and that they should have a relatively low effect on throughput.

The IMC plus persistent storage option may provide the most comprehensive solution for RDD of substantially weak defects and soft repeater defects with substantially modest requirements for new HW. The change of the architecture includes collecting all defect coordinates in the shared memory and full defect information on persistent storage that may be reused for other applications, e.g., detect classification in IMC, defect sampling, etc.

In an additional embodiment, the one or more image processing components include a shared non-transitory computer-readable storage medium accessible for multiple processes performed by the one or more image processing components, the one or more image processing components are configured for storing only a first portion of results produced by the RDD algorithm in the shared non-transitory computer-readable storage medium, the first portion includes only defect coordinates for the defects detected on the wafer, the RDD algorithm is configured to identify the repeater defects using only the first portion of the results, the interface component is configured for controlling the one or more HW elements of the inspection subsystem to thereby scan only locations on the wafer of the identified repeater defects, and the one or more image processing components are configured for combining images generated in the scan of only the locations on the wafer of the identified repeater defects with the first portion of the results to thereby generate the inspection results that are sent to the interface component.

In this manner, the embodiments described herein may be configured for two pass RDD. This approach utilizes half of the split DB. Defect candidates may be detected and only their coordinates are stored in the shared memory. In particular, in a first pass, no defects are returned to the Main UI. Instead, defect coordinates and some extra information is saved in the shared memory. The shared memory contains coordinates of all defects. This data is used for RDD. In particular, a new executable may be used to perform RDD using the saved coordinates. Coordinates of the repeater defects are saved in the shared memory. Therefore, the shared memory will contain repeater defect coordinates at that step.

In order to get defect images and compute attributes, the wafer is scanned for the second time only in the locations where the repeaters were found. For example, in the second pass, one or more components of the computer subsystem(s) will read repeater defect coordinates from the shared memory. The one or more components may then convert these locations into "forced defects." The IMC may then compute defect attributes, extract patch images, apply a nuisance filter, and return the die repeaters to the Main UI.

The Main UI may then perform reticle-level repeater defect analysis as described further herein and assign repeater ID. In this manner, the embodiments described herein may be configured for splitting the defect data for RDD and defect attributes calculation/reporting.

The embodiment described above minimizes HW cost by trading it off with a throughput reduction. This solution may be most advantageous for development of production worthy recipes and systems. In addition, the two pass inspection configuration may be a preferred solution for demonstration/testing the sensitivity (with a VI implementation) that can be deployed at user sites.

The embodiment described above is similar to the "split DB" (IMC with persistent storage) approach, but storing the candidate data is skipped. Defect detection jobs will save defect coordinates in shared memory and skip patch extraction and defect attributes calculation altogether. After wafer swathing is performed, job manager SW may issue RDD jobs that will find repeater defects among the saved defect candidates. The repeater defect coordinates are returned to the interface component (and most likely Main UI) and "discrete location inspection" or "forced defect" jobs are issued for these locations. The IMC may return defect patch images and defect attributes for repeater locations. The system can also be simplified by saving RDD job results in the shared memory and using normal defect detection jobs for the second pass. In this case, the IMC will read corresponding files with repeater coordinates and either convert defect detection jobs into forced defect jobs or return empty result buffer.

In a further embodiment, the RDD algorithm is configured to identify the defects that appear at the same location in two or more printed instances of the reticle on the wafer as the repeater defects. Identifying the defects that appear at the same location in two or more printed instances of the reticle may be performed as described further herein. For example, the RDD algorithm may identify the defects that appear at the same location in printed instances of the reticle on the wafer as described further herein based on the reticle coordinates of the defects. When two or more defects are detected on the wafer at the same within reticle coordinates in different printed instances of the reticle on the wafer, the defects may be determined to be reticle repeater defects.

In some embodiments, identifying the defects on the reticle is performed by the main user interface component included in the one or more computer subsystems. For example, as described further herein, the Main UI of the computer subsystems) may be configured to identify the defects on the reticle. However, depending on the particular configuration and intended use of the system, one or more other components of the computer subsystem(s) may be configured to perform this identifying step.

The embodiments described above have, therefore, a number of advantages over currently used methods and systems for RDD. For example, the new approaches described above allow for increased sensitivity for repeater defects. Increased sensitivity for RDD is important for a number of applications. In one example, the introduction of extreme ultraviolet (EUV) lithography processes into semiconductor manufacturing requires frequent mask inspection (these masks are more susceptible to defects because the masks do not have pellicles and may be exposed during operation) and moves the operation from the mask inspector (there are no mask inspectors with actinic light for EUV) to the wafer inspector. Repeater defects for EUV are expected to be substantially small and/or weak and may be printed only on several dies on the wafer. In order to find such defects, the wafer inspector has to process huge numbers of candidate defects, which cannot be done with the current approaches. In addition, the introduce of EUV lithography raises the necessity for robust detection of repeater defects.

In another example, printable systematic defects for the 7 nm design rule (DR) are substantially small (e.g., about 3 nm defects), so in order to catch such defects, the inspections have to be run substantially hot. Repeater detection (coordinates matching) is a substantially strong filter that can be used to reduce the nuisance density to manageable levels, but the problem is the current RDD algorithm is executed in the Main UI and prior to running RDD, all wafer defects must be collected. Hot inspections required for mask qualification result in millions of defect candidates (prior to RDD) that cause tool choking and dropped defects when transferring results from the IMC to the interface component and from the interface component to the Main UI. RDD is subject to the same limitations of maximum number of defects and defect density as random defect detection inspection, although the final number of DOIs (repeaters) may be reasonably small. It should be noted that many repeater defects are "soft" repeaters—they are not printed in every reticle due to process variation. This means that we cannot use in-job RDD and have to be able to analyze the whole wafer results. The embodiments described herein provide several new mechanisms for RDD thereby overcoming these limitations.

The embodiments described herein are also based on the substantially high accuracy of the defect locations available for performing RDD (e.g., accuracy better than +/−0.5 pixel) and assume sub-pixel accuracy alignment. It is assumed that repeater coordinates can be used as a substantially strong filter that will suppress a majority of the random defects in a substantially hot inspection allowing the use of substantially low thresholds. It is further assumed that repeaters are detectable by at least one of the available defect detection algorithms. Of course, if the defect is deep in the noise floor, the problem shifts from RDD to normal defect detection space. The embodiments described herein are also configured for multi-die reticle inspection. If the reticle is a single die reticle, standard reference die (SRD) inspection should be used since in this case repeater defects will be printed in every die and cannot be found by traditional die-to-die comparisons.

Results similar to those described herein might be achieved by increasing the internal network bandwidth, results storage space, and computational power of the Main UI computer. However, such work around solutions do not provide many of the advantages described herein.

As described above and further herein, the embodiments provide substantially high sensitivity repeater analysis, which improves defect detection sensitivity. Currently used methods for defect detection use double detection to detect defects as it is crucial to find out if defects are in the test or the reference image. The reference images are the adjacent dies of the defective die. Current repeater analysis techniques are limited by not being able to run hot enough which limits sensitivity. Therefore, the currently used methods are too insensitive. In addition, if a reference image is too defective, defects will not be detected at all.

In one embodiment, the RDD algorithm is configured to detect the defects by generating three or more difference images for each test frame of the images generated for the wafer by subtracting three or more reference frames from the test frame, respectively, applying at least one threshold to the three or more difference images, and determining that a defect is present in the test frame when results of two or more of applying the at least one threshold to the three or more difference images indicate that a defect is present. In this manner, each frame may be compared to several reference frames, for example, to six reference frames instead of currently two. If at least two difference frames suggest that there is a defect, the candidate frame can be assumed to be defective.

Figure 4:
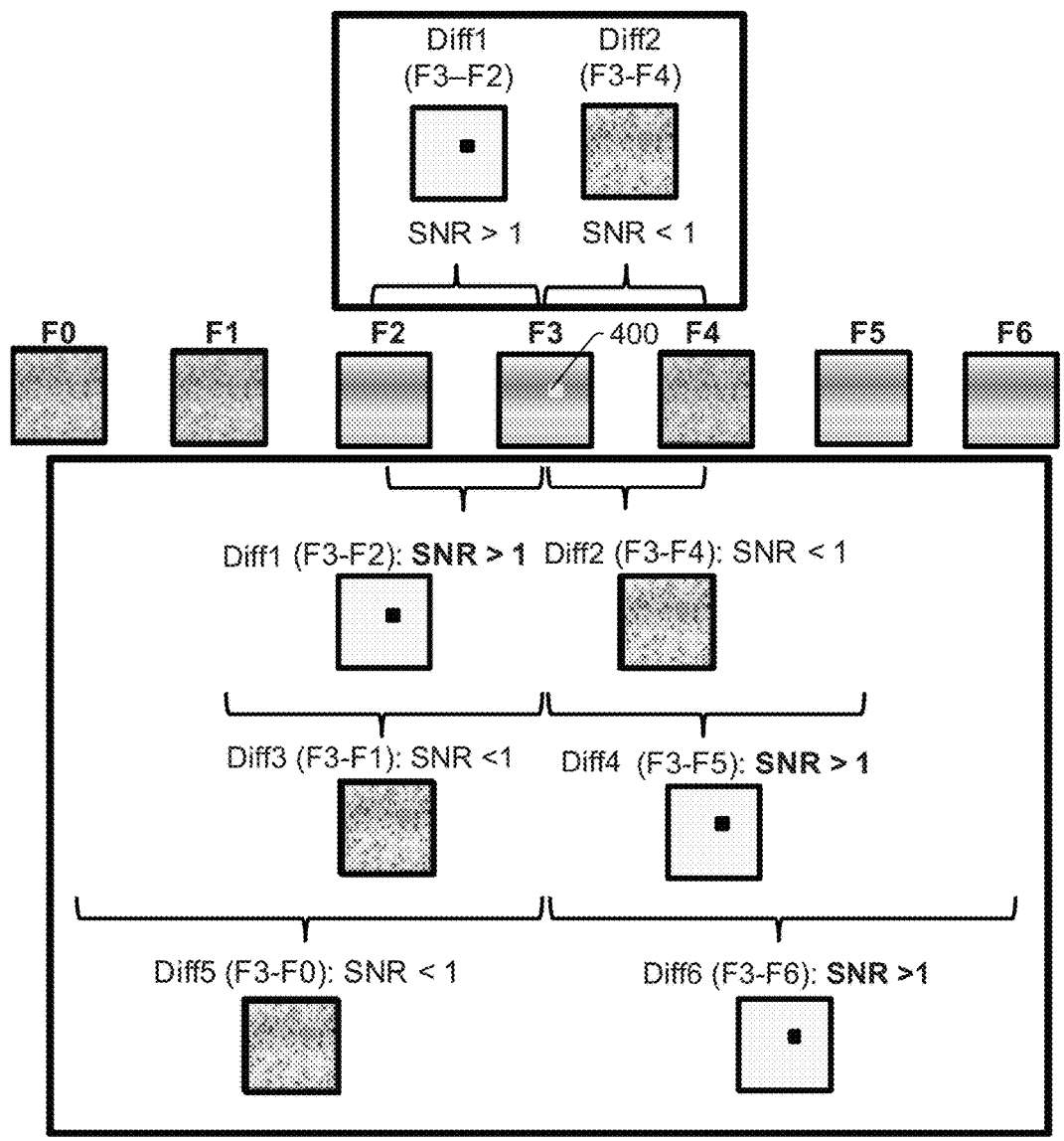
FIGS. 4-8 are schematic diagrams illustrating various embodiments of steps that may be performed by the system embodiments described herein.

FIG. 4 shows an embodiment of how this defect detection can be performed. Frames F0, F1, F2, F3, F4, F5, and F6 shown in this figure represent different image frames that may be generated for a wafer by art inspection subsystem described herein. In the current implementation, one of the frames may be compared to two other frames in a double detection scheme, and if a defect is detected in both results of the comparisons, then a defect is determined to be present. For example, a first difference image (Diff1 shown in FIG. 4) may be generated by subtracting frame F2 from frame F3. In addition, a second difference image (Diff2 shown in FIG. 4) may be generated by subtracting frame F4 from frame F3. Therefore, in these comparisons, frame F3 is the test frame, and frames F2 and F4 are used as the reference frames. If these two difference images are used for defect detection, then defect 400 will not be detected. In particular, as shown in FIG. 4, defect 400 in frame F3 appears in Diff1 but not Diff 2 because of the different noise characteristics of frame F4 compared to frames F2 and F3. In this manner, the current implementation of double detection will miss that defect because it is not double detected in both difference images.

In the embodiments described herein, however, if frame F3 is the test frame, then it may be compared to each of the other frames shown in FIG. 4 and the results of each of these comparisons may be used to determine if a defect is present in frame F3. For example, like the currently used methods, a first difference image (Diff 1 shown in FIG. 4) may be generated by subtracting frame F2 from frame F3, and a second difference image (Diff 2 shown in FIG. 4) may be generated by subtracting frame F4 from frame F3. However, additional difference images may be generated in this embodiment including a third difference image (Diff3 shown in FIG. 4) that is generated by subtracting frame F1 from frame F3 and a fourth difference image (Diff4 shown in FIG. 4) that is generated by subtracting frame F5 from frame F3. In addition, a fifth difference image (Diff5 shown in FIG. 4) may be generated by subtracting frame F0 from frame F3, and a sixth difference image (Diff6 shown in FIG. 4) may be generated by subtracting frame F6 from frame F3. A defect may be determined to be present in the test frame if a defect signal in two or more of the difference images is above a threshold. For example, the threshold may be set to 1. In this case, as shown in FIG. 4, Diff1, Diff4, and Diff6 have a signal-to-noise ratio (SNR) greater than 1 while Diff2, Diff3, and Diff5 do not have a SNR greater than 1. Therefore, since two or more of the difference images (in this case three difference images) have an SNR above the threshold, it is determined that a defect is present in the test frame.

Figure 5:
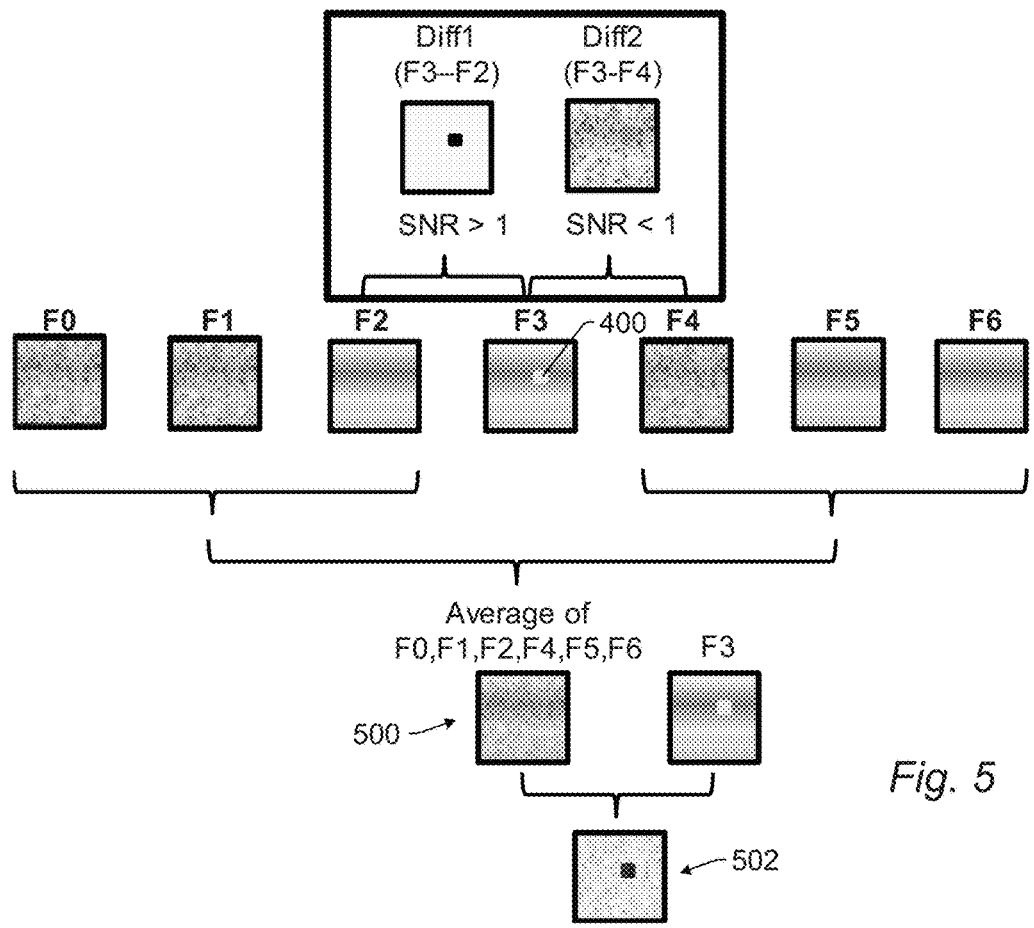

In a further embodiment, the RDD algorithm is configured to detect the defects by comparing each test frame of the images generated for the wafer to an average of multiple reference frames. In this manner, each frame may be compared to an average (e.g., a robust average) of multiple reference frames. FIG. 5 shows an embodiment of how this defect detection can be performed. Frames F0, F1, F2, F3, F4, F5, and F6 shown in this figure represent different image frames that may be generated for a wafer by an inspection subsystem described herein and are the same as those shown in FIG. 4.

In the current implementation, one of the frames may be compared to two other frames in a double detection scheme, and if a defect is detected in both results of the comparisons, then a defect is determined to be present. For example, a first difference image (Diff1 shown in FIG. 5) may be generated by subtracting frame F2 from frame F3. In addition, a second difference image (Diff2 shown in FIG. 5) may be generated by subtracting frame F4 from frame F3. Therefore, in these comparisons, frame F3 is the test frame, and frames F2 and F4 are used as the reference frames. If these two difference images are used for defect detection, then defect 400 (the same defect as shown in FIG. 4) will not be detected. In particular, as shown in FIG. 5, defect 400 in frame F3 appears in Diff1 but not Diff 2 because of the different noise characteristics of frame F4 compared to frames F2 and F3. In this manner, the current implementation of double detection will miss that defect because it is not double detected in both difference images.

In the embodiments described herein, however, Average 500 shown in FIG. 5 of frames F0, F1, F2, F4, F5, and F6 may be generated. In this manner, an average frame may be generated from all of the available reference frames (e.g., all of the frames other than frame F3 which is being used as the test frame in the embodiment shown in FIG. 5). The average frame may then be subtracted from the test frame F3 to generate difference image 502, A threshold may then be applied to the difference image as described further herein to thereby detect defect 400. As such, in this embodiment, a candidate or test frame can be compared to an average of reference frames and the results of the comparison can be used to detect defects in the candidate or test frame.

Figure 6:
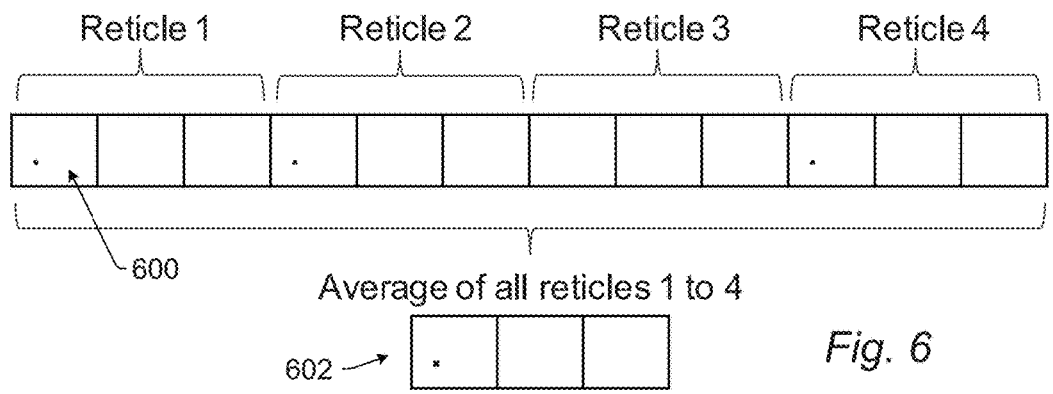

In an additional embodiment, the RDD algorithm is configured to detect the defects by generating a mean of multiple frames of the images generated for the wafer corresponding to the same location within each reticle instance printed on the wafer and subtracting the mean from reference frames from dies on the wafer at different locations within multiple reticle instances printed on the wafer. In this manner, in the case of hard repeater defects (which occur on every reticle on the wafer), the mean of several image frames of the same location within each reticle can be calculated and subtracted from reference frames from dies at different locations within the reticles. For example, as shown in FIG. 6, different instances of a reticle, a multi-die reticle in this case, can be printed on a wafer. Those printed instances of a reticle are indicated in FIG. 6 as Reticle 1, Reticle 2, Reticle 3, and Reticle 4, each of which is a different printed instance of the same reticle on the wafer. As further shown in FIG. 6, each of the printed reticle instances includes multiple dies 600, all of which are usually the same. In this case, each reticle includes three dies, each of which are printed on the wafer for each instance of the reticle.

Average 602 (or mean) can be generated for these printed instances of the reticle. For example, average 602 can be generated from all of reticles 1 to 4 as shown in FIG. 6. The average reticle may be determined from all of the printed instances of the reticle on the wafer. However, the average reticle may be determined from fewer than all of the printed instances of the reticle on the wafer. The frames in the average of the reticles can then be subtracted from many different, corresponding reference frames. In this manner, a test frame in the average reticle can replace test Frame 3 in FIG. 4 and then the steps described herein with respect to FIG. 4 can be performed for the test frame in the average. If at least two of the difference images have a SNR greater than 1, the test frame can be considered to contain a defect. All of the test frames in the average reticle can be used for defect detection in the same manner.

In one embodiment, the RDD algorithm is configured to detect the defects by generating a mean of multiple frames of the images generated for the wafer corresponding to the same location within each reticle instance printed on the wafer and subtracting the mean from a mean of reference frames from other dies at different locations within multiple reticle instances printed on the wafer. In this manner, in the case of hard repeater defects (which occur on every reticle on the wafer), the mean of several image frames of the same location within each reticle can be calculated and subtracted from a mean of reference frames from other dies at different locations within the reticles. In this embodiment, the mean may be generated as described in the above embodiment. The frames in the average of the reticles can then be subtracted from a mean or median of different, corresponding reference frames. In this manner, a test frame in the average reticle can replace test Frame 3 in FIG. 5 and then the steps described herein with respect to FIG. 5 can be performed for the test frame in the average. If the difference image has an SNR greater than 1, it can be considered to contain a defect. All of the test frames in the average reticle can be used for defect detection in the same manner.

In another embodiment, the RDD algorithm is configured to identify the defects that are the repeater defects by adding image frames corresponding to a location of a detected defect in multiple instances of the reticle printed on the wafer, comparing the added image frames to a threshold, and determining that the defect is a repeater defect when the added image frames are above the threshold. For example, in the case of soft repeater defects (which occur on only some reticle instances printed on the wafer), combinations of candidate frames (same location within several reticles) can be added, e.g., in one scenario reticles 1, 4, and 5 are added, in another one 1, 3, and 6 are added, and so on. Adding the reticles may be performed in a frame-wise manner in which the raw frames in each (or more than 2) reticles are added. Adding the candidate frames may include adding the raw pixel output for the candidate frames. If one combination has a pixel with a high enough SNR, e.g., higher than a detection threshold, it can be concluded that there is a repeater defect. For example, as shown in FIG. 6, different instances of a e.g., Reticle 1, 2, 3, and 4, may be printed on a wafer. Different of these printed instances can then be added for defect detection.

In some embodiments, the RDD algorithm is configured a) to detect the defects and to identify the defects that are the repeater defects in only a first swath by identifying the defects that appear at the same location in a first number of instances of the reticle printed on the wafer as the repeater defects and b) to subsequently detect the defects and to identify the defects that are the repeater defects in other swaths by identifying the defects that appear at the same location in a second number of instances of the reticle printed on the wafer as the repeater defects, and the second number is higher than the first number. In this manner, in the case of relatively low signal repeater defects for which one needs to run substantially hot, a two pass repeater analysis can be performed. The first pass is based on one single swath to reduce the number of defects to a reasonable number, and the second pass operates on (performs repeater analysis with a higher repeater threshold for) all swaths which went through pass 1 for the entire wafer.

In one such example, initially, one million defects may be detected per swath but most of them do not have the same reticle coordinates. The number of defects can be reduced by performing a reticle repeater analysis on this swath only, and all of the defects that do not occur at least two times at the same reticle coordinates (within the same repeater radius or "tolerance" described further herein) get filtered out. In the end, a substantially smaller number of defects (e.g., only 10,000 defects) remain per swath which reduces the required storage space significantly.

Figure 7:
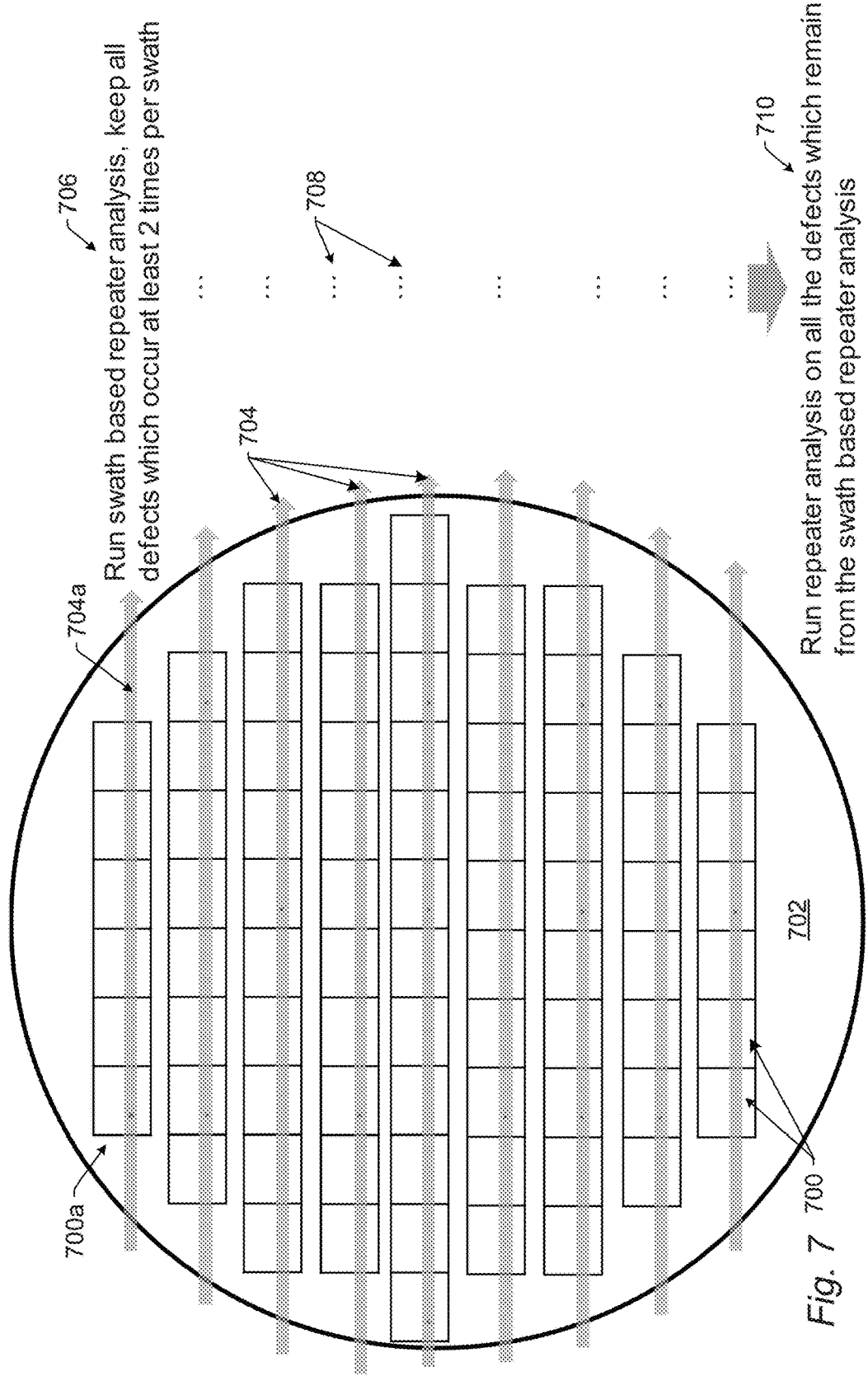

After such repeater analysis has been performed for every swath, a full wafer repeater analysis can be performed with a higher repeater threshold (e.g., 20 repeaters with the same reticle coordinates) to further reduce the number of reported repeaters. For example, as shown in FIG. 7, multiple dies 700 may be formed on wafer 702. As the inspection subsystem (not shown in FIG. 7) scans over the wafer thereby generating images for the wafer, swaths 704 of images are generated for the wafer. In general, the swaths of the image data are shown in FIG. 7 overlaid with their corresponding positions on the wafer. In this manner, although the swaths are just images generated by a detector for some area on the wafer, the swaths are often referred to as swaths on a wafer even though they are not actually on the wafer. In any case, the area to be inspected on the wafer is generally scanned swath-by-swath, until images have been generated for the entire inspection area. However, the swaths of image data can be processed before all of the swaths of image data have been acquired.

For example, as shown in FIG. 7 and described further above, swath 704*a* can be acquired in first die row 700*a* on wafer 702. As the swath is being scanned or after this swath has been acquired and before other swaths have been acquired, as shown in step 706, the IMC may run swath-based repeater analysis, and keep all defects that occur at the same within reticle position at least two times per swath. This step can then be performed for all of the other swaths on the wafer as shown by ellipses 708 in FIG. 7. After all of the swaths (or as many of the swaths as desired) have been processed for swath-based repeater analysis, as shown in step 710, repeater analysis can be run on all the defects that remain from the swath based repeater analysis.

In one such embodiment, the RDD algorithm s configured to reduce noise in the first swath by filtering out systematic noise that occurs in every instance of the reticle printed on the wafer in the first swath and at the same location in each die instance of the reticle printed on the wafer in the first swath. For example, additional noise reduction in the first pass repeater analysis can be achieved by filtering out systematic noise that occurs in every reticle and at the same location in every die. In one such example, if the noise always occurs on the exact same structure, for example, an edge of a certain polygon or at the same location in every die, then it is called systematic noise. In contrast, repeater defects only occur once per reticle but not once per die or multiple times per die.

In one embodiment, the RDD algorithm is configured to detect the defects by comparing image frames of reticle instances printed on the wafer to a standard image frame generated from a different wafer. For example, the image frames of every reticle on a candidate wafer can be compared to a standard reticle printed on a clean wafer. The image of the standard reticle printed on a clean wafer can be acquired in any suitable manner. The standard reticle image can be determined to be from a clean wafer in any suitable manner. For example, the standard reticle image can be acquired by finding a reticle image that is substantially defect free. In some instances, the standard reticle image may be acquired by printing the reticle on a wafer of the same type as will be inspected by embodiments described herein with a known good process (a process known to be functioning within the process window for the process). The various instances of the reticle on the wafer can then be examined for defects as in a standard defect detection process. An instance of the reticle that is found to be defect free can then be used as the standard reticle. The image frames of reticle instances printed on the wafer can be compared to the standard image frame as described herein (e.g., by subtracting one from the other), and a defect detection threshold can be applied to the results of the comparison (e.g., difference images) to thereby detect defects on the wafer.

In another embodiment, the RDD algorithm is configured to detect the defects by comparing image frames of reticle instances printed on the wafer to a median image frame generated from a different wafer. For example, the image frames of every reticle on a candidate wafer can be compared to a median reticle printed on a clean wafer. The clean wafer may be a wafer of the same type as that inspected by the embodiments described herein printed with a known good process (a process known to be functioning within the process window for the process) and a defect free version of the reticle. The median image frame may be generated from the different wafer as described further herein. The image frames may be compared to the median image frame as described further herein. In addition, the results of these comparisons may be used as described further herein to detect defects on the wafer.

In an additional embodiment, the RDD algorithm is configured to detect the defects by comparing image frames of reticle instances printed on the wafer to a rendered design. For example, the image frames of every reticle on a candidate wafer can be compared to rendered design, The rendered design may be a simulated image of the reticle that illustrates how the reticle printed on the wafer would appear in images generated by the inspection subsystem. Therefore, the rendered design may be generated using the design for the wafer as input to a model of the lithography process and the inspection subsystem imaging process. The rendered design may be also generated as described in U.S. Pat. No. 7,689,966 issued on Mar. 30, 2010 to Verma et al., U.S. Patent Application Publication Nos. 2017/0148226 published May 25, 2017 by Zhang et al., 2017/0193680 published Jul. 6, 2017 by Zhang et al., 2017/0194126 published Jul. 6, 2017 by Bhaskar et al,, 2017/0200260 published Jul. 13, 2017 by Bhaskar et al., and 2017/0200265 published Jul. 13, 2017 by Bhaskar et al., and U.S. patent application Ser. No. 15/603,249 filed May 23, 2017 by Zhang et al., Ser. No. 15/694,719 filed Sep. 1, 2017 by Zhang et al., and Ser. No. 15/697,426 filed Sep. 6, 2017 by He et al., which are incorporated by reference as if fully set forth herein. The embodiments described herein may be further configured as described in these publications and applications. The image frames may be compared to the rendered design as described further herein, and the results of the comparisons may be used to detect the defects as described further herein.

In a further embodiment, the hot threshold includes a local multiple die adaptive threshold. For example, in order to run substantially hot, a local multi-die adaptive threshold algorithm can be used. The local multi die adaptive threshold algorithm may include any suitable such algorithm known in the art including the multi-die automatic thresholding (MDAT) algorithm and the nanoMDAT algorithm that are available on some inspection systems commercially available from KLA-Tencor.

In one embodiment, the one or more image processing components are configured for storing information for the detected defects in shared memory per node of the one or more image processing components. For example, in order to run very hot, in node repeater analysis can be used, which means that the information for the defects is processed internally without reporting the detected defects and only the repeaters are reported in the end. In this configuration, defects can be saved in (shared) memory per IMC node. A certain storage space per node can be reserved which should allow for storing more than 100 million defects.

Figure 9:
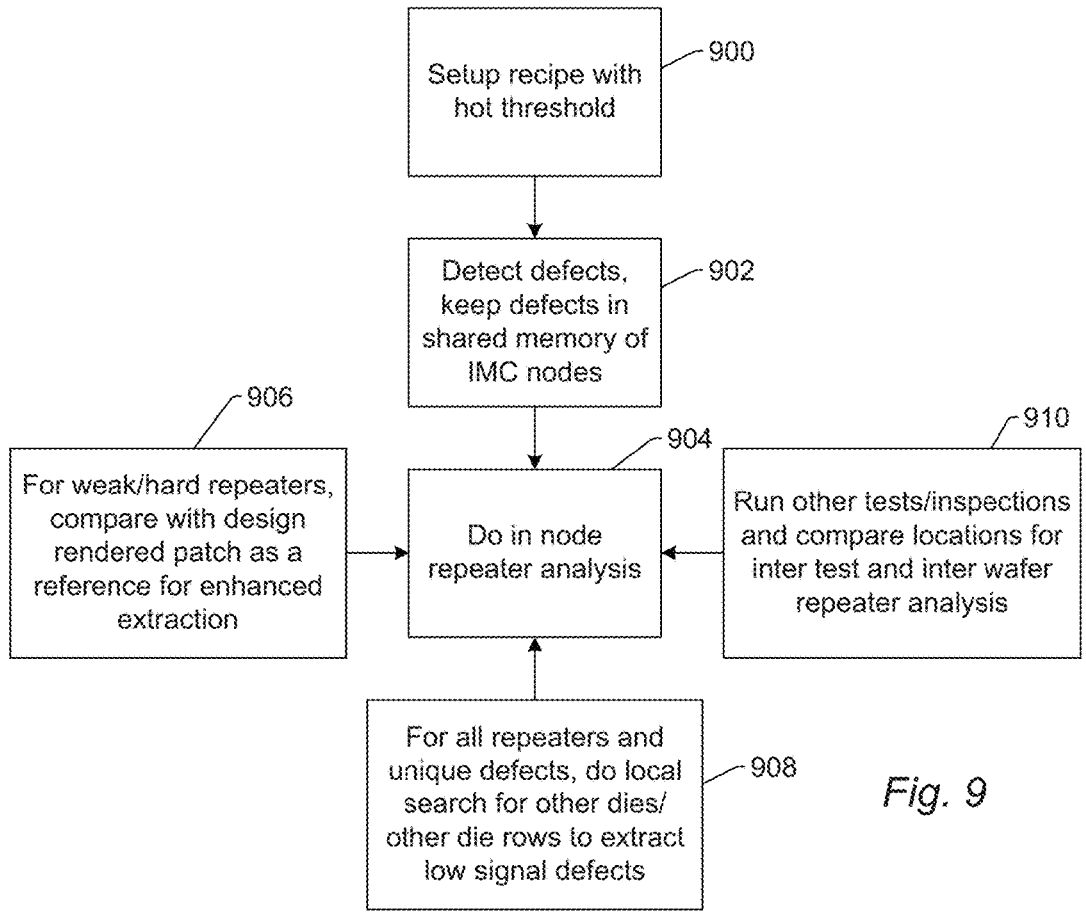
FIG. 9 is a flow chart illustrating one embodiment of steps that performed by the system embodiments described herein.

In one such embodiment, as shown in FIG. 9, the one or more computer subsystems may setup a recipe with a hot threshold, as shown in step 900. Setting up the recipe with the hot threshold may be performed in any suitable manner known in the art. The IMC may then, as shown in step 902, detect defects on the wafer and keep defects in the shared memory of the IMC nodes. This step may be performed as described further herein. As shown in step 904, the IMC may then do in node repeater analysis, which may be performed as described further herein.

Figure 8:
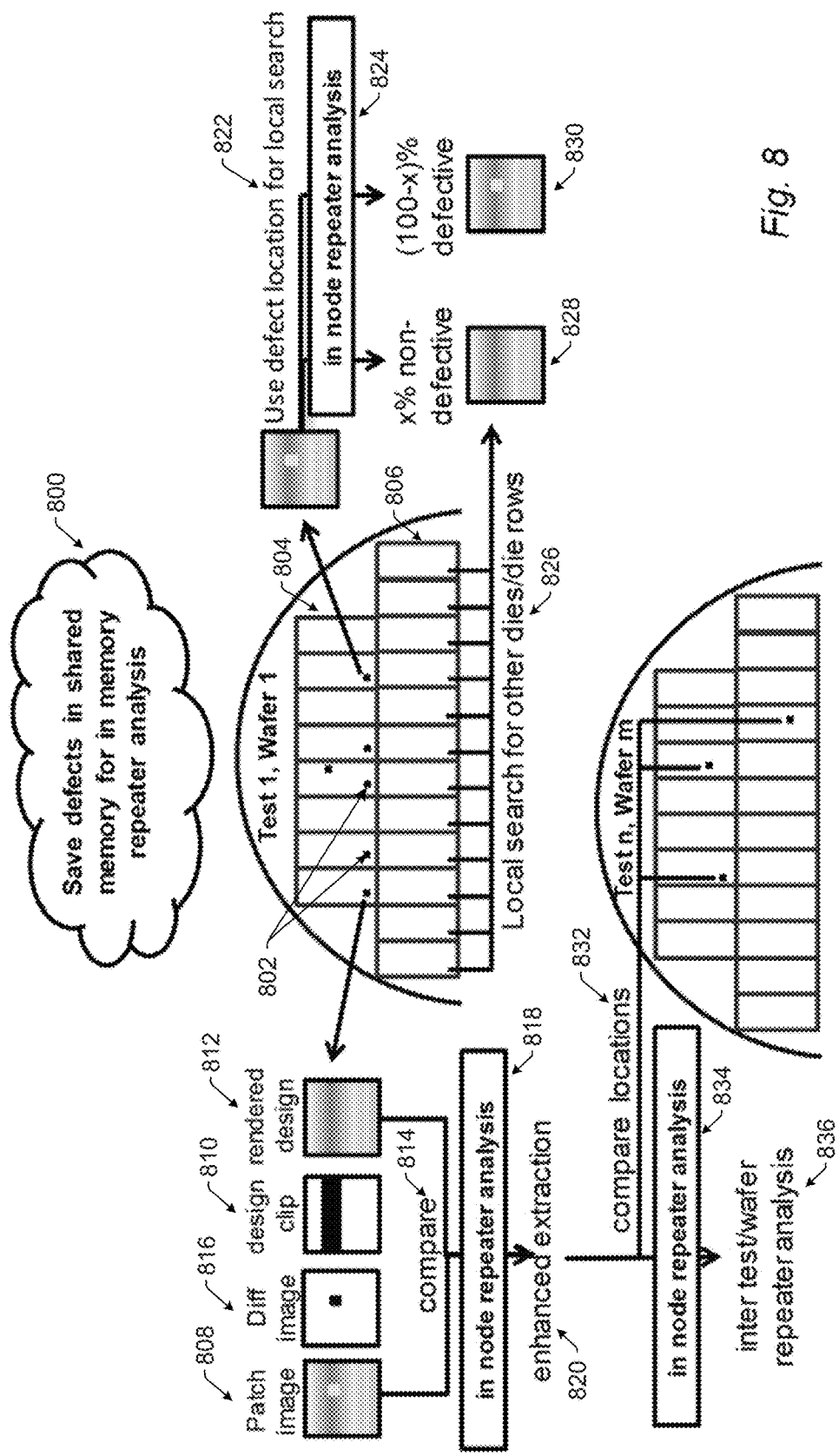

In one such embodiment, the information stored for the detected defects in the shared memory includes information for only defects detected in one or more first die rows on the wafer. The first die rows are the die rows that are scanned first. In this manner, defects of the first die rows may be saved in shared memory. For example, as shown in FIG. 8, the IMC may save defects in shared memory for in memory repeater analysis, as shown in step 800. The defects that are saved in the shared memory for in memory repeater analysis may include defects 802 detected in test 1 on wafer 1. The defects that are saved in the shared memory may also include only defects detected in single die row 804 on the wafer or in multiple die rows 804 and 806 on the wafer. Although the single die row is shown as a particular die row on the wafer, the single die row may include any single die row on the wafer. In addition, the multiple die rows on the wafer may include all of the die rows on the wafer or only some of the die rows on the wafer (e.g., two or more die rows on the wafer).

The embodiment shown in FIG. 9 may include any other step(s) described herein. For example, as shown in step 906, for weak and/or hard repeaters, the IMC may compare the image frames with design rendered patches as a reference for enhanced extraction. This step may be performed as described further herein. In one such embodiment, as shown in FIG. 8, patch image 808 may be acquired for wafer 1. Design clip 810 may be acquired for the portion of the design corresponding to the patch image. In this manner, any design features that are in that design clip should correspond to the design features formed on the portion of the wafer at which the patch image was acquired. The design clip may then be rendered to thereby generate rendered design 812, which simulates how the design clip would be formed on the water and then imaged by the inspection subsystem. Such simulations may be performed in any suitable manner known in the art. In this manner, the rendered design should be equivalent to an image generated by the inspection subsystem of a portion of the wafer in which the design features in the design clip were formed. As such, the rendered design is equivalent to a defect free image of the portion of the wafer corresponding to the design clip. Therefore, the rendered design can be used as a reference for comparison to a test image, e.g., patch image 808, to detect defects in the test image. For example, rendered design 812 can be compared, as in step 814, to patch image 808 by subtracting the rendered design from the patch image thereby generating difference image 816. These steps may be performed for in node repeater analysis 818 for enhanced extraction 820 of weak and/or hard repeater defects.

In some such embodiments, the RDD algorithm is configured to identify the defects that are the repeater defects by identifying defects detected in adjacent dies in the one or more first die rows at the same die relative locations as the repeater defects and identifying defects not detected in the adjacent dies in the one or more first die rows at the same die relative locations as non-repeater defects. In this manner, defects from adjacent dies on the same die row at the same (or close within tolerance) die relative location will be compared and repeaters and unique defects will be marked. These steps may be performed as described further herein.

In one such embodiment, the RDD algorithm is configured to identify the defects that are the repeater defects by identifying defects detected in adjacent dies in other die rows on the wafer at the same die relative locations as the repeater defects and identifying defects not detected in the adjacent dies in the other die rows at the same die relative locations as non-repeater defects. For example, defects in subsequent die rows will be compared, and repeaters and unique defects will be marked. For example, the defects in the subsequent die rows may be compared in terms of their die coordinates. If the die coordinates are the same for a certain number of defects, those defects can be designated as repeater defects. These steps may be performed as described further herein.

In one such embodiment, the RDD algorithm is configured to identify the defects that are the repeater defects by extracting portions of the images generated for the wafer at the same die relative locations as the non-repeater defects and applying a local defect detection algorithm to the extracted portions of the images to thereby determine if undetected defects repeat at the same die relative locations as the non-repeater defects. For example, for unique defects, an additional (local) defect detection algorithm may be applied to extract weak defect signals from the same location for other dies/die rows. In one such embodiment, as shown in FIG. 9, the IMC may perform step 908 in which, for all repeaters and unique defects, a local search is done for other dies/other die rows to extract low signal defects.

in this step, as shown in FIG. 8, a defect location of one of defects 802 detected in die row 804 on wafer 1 may be used as a defect location for local search, as shown in step 822. This step may be performed for in node repeater analysis 824 in which for all repeaters and unique defects, as shown in step 826, a local search is performed for other dies and/or die rows. In this manner, relatively low signal defects can be extracted. In addition, by examining multiple (or all) of the locations corresponding to a defect location, the IMC may determine the x % non-defective locations 828 and the (100-x)% defective locations 830. These percentages can be used to determine information about the defects (are they soft repeaters?, are they hard repeaters? are they weak soft repeaters?, etc.).

As shown in step 910 in FIG. 9, the IMC may run other tests/inspections and compare locations for inter test and inter wafer repeater analysis. For example, as shown in step 832 of FIG. 8, defects detected by enhanced extraction 820 with images generated by Test 1 performed for Wafer 1 could be used to compare locations with images and/or defects detected by Test n on Wafer m. Defects detected in any other way described herein may also be used for such comparisons. Those comparisons may then be used for in node repeater analysis step 834, which is performed for inter test and/or inter wafer repeater analysis 836. In this manner, the embodiments described herein can be used to determine if defects repeat at the same location from test to test performed on the same wafer and/or from wafer to wafer.

In the embodiments described herein, one could accumulate all defect candidates in the IMC memory up to the end of wafer inspection. Normal defect detection may be run, a "no defects" result buffer may be returned to the interface component, and all defect candidates may be stored in the shared memory. For example, currently, every defect that is detected is reported. However, here it is much more efficient to not report any defects before repeater analysis is performed, which is a substantially efficient way to store defect coordinates. In addition, hot inspections may be run saving all defect candidates on a VI. On the VI, inspection may be run to find repeaters using defect coordinates and returning defect locations, attributes, and patches to the Main UI. Furthermore, as described further herein, only repeater coordinates but no patch images may be saved.

In another embodiment, the RDD algorithm is configured to align the images generated for the wafer to a design for the wafer with sub-pixel accuracy. For example, design based sub-pixel accuracy alignment allows for using a substantially small repeater radius allowing substantially efficient nuisance filtering. Aligning the images generated for the wafer to a design with sub-pixel accuracy may be performed as described in U.S. Pat. Nos. 7,676,077 issued on Mar. 9, 2010 to Kulkarni et al., U.S. Pat. No. 8,041,103 issued on Oct. 18, 2011 to Kulkarni et al., U.S. Pat. No. 8,139,843 issued on Mar. 20, 2012 to Kulkarni et al., and U.S. Pat. No. 9,134,254 issued on Sep. 15, 2015 to Ramachandran, and U.S. Patent Application Publication Nos. 2016/0188784 published on Jun. 30, 2016 by Bhattacharyya et al., which are incorporated by reference as if fully set forth herein. The embodiments described herein may be further configured as described in these patents and publications.

In a further embodiment, the RDD algorithm is configured to determine which of the repeater defects are defects of interest and Which of the repeater defects are nuisances using a machine learning technique performed based on attributes of the repeater defects, properties of the images corresponding to the repeater defects, or a combination thereof. For example, further nuisance reduction can be achieved by separating defects of interest (DOIs) and nuisances using machine learning type techniques that either use existing defect attributes or image based properties to separate DOI from nuisance. Examples of such machine learning type techniques are described in U.S. Patent Application Publication Nos. 2017/0148226 published May 25, 2017 by Zhang et al., 2017/0193680 published Jul. 6, 2017 by Zhang et al., 2017/0194126 published Jul. 6, 2017 by Bhaskar et al., 2017/0200260 published Jul. 13, 2017 by Bhaskar et al., and 2017/0200265 published Jul. 13, 2017 by Bhaskar et al., and U.S. patent application Ser. No. 15/603,249 filed May 23, 2017 by Zhang et al., Ser. No. 15/694,719 filed Sep. 1, 2017 by Zhang et al., and Ser. No. 15/697,426 filed Sep. 6, 2017 by He et al,, which are incorporated by reference as if fully set forth herein. The embodiments described herein may be further configured as described in these publications and patent applications, In an additional embodiment, the RDD algorithm is configured to align the images generated for the wafer to each other by identifying a common alignment target in two portions of the images processed by the RDD algorithm as two different jobs, respectively, aligning the two different jobs to each other using the common alignment target, determining an alignment offset based on results of the aligning, and applying the alignment offset to other jobs to thereby align the other jobs to the two different jobs, In one such embodiment, the two different jobs are located in different die rows on the wafer. For example, if a design file cannot be used tor alignment due to intellectual property constraints or there are not enough good alignment targets in it, one job can be extended to one entire die row, i.e., one single swath ranging from the left side to the right side of the wafer. In this manner, all the image frames with the same die coordinates can be well aligned to each other within the one single swath. Currently, one job may contain up to a maximum number of frames, e.g., 12 frames. So extending the job may include using many more frames for a job so that all of the frames within one die row are aligned to each other. For example, if there are 25 frames, meaning there are 25 dies in one swath, then all of these frames will be very well aligned to each other. In addition, two jobs of different die rows can be aligned with respect to each other by finding a common alignment object in the two job files, aligning those to each other, and applying the calculated offset to all sites within the job. These steps may be performed in any suitable manner.

The embodiments described herein have, therefore, a number of advantages over currently used methods and systems. For example, the embodiments described herein provide higher sensitivity than currently used methods and systems. In one such example, the sensitivity of repeater detection is enhanced by using a variety of reference frame combinations and a defect storage model that allows to run much more into the noise floor. In addition, the embodiments described herein do not have a sensitivity that is limited when performing repeater analysis on a full wafer due to the limitation of the total number of defects that can be handled by the system or method. The embodiments described herein also allow finding defects with relatively low signal on noisy wafers. Furthermore, using the embodiments described herein during inspection will improve sensitivity to key DOI. In another example, the embodiments described herein are able to run much hotter than currently used methods and systems. In an additional example, the embodiments described herein enable comparisons that are not limited to just one reference. In a further example, the embodiments described herein provide a lower nuisance rate than currently used methods and systems.

Each of the embodiments of the system described herein may be combined with any other embodiments of the system described herein.

Another embodiment relates to a computer-implemented method for detecting defects on a reticle. The method includes acquiring images generated for a wafer by an inspection subsystem. A reticle is used to print features on the wafer in a lithography process. The acquiring is performed by one or more image processing components included in one or more computer subsystems. The one or more computer subsystems include a main user interface configured for providing information generated for the wafer and the reticle to a user and for receiving instructions from the user. The one or more computer subsystems also include an interface component configured for providing an interface between the one or more image processing components and the main user interface component and for controlling one or more HW elements of the inspection subsystem. The method also includes performing RDD by applying an RDD algorithm to the images acquired by the one or more image processing components. The RDD algorithm is configured to detect defects on the wafer using a hot threshold and to identify the defects that are repeater defects. The RDD is performed by the one or more image processing components. In addition, the method includes sending inspection results that include information for only the repeater defects from the one or more image processing components to the interface component. The method further includes identifying defects on the reticle based on the repeater defects detected on the wafer. Identifying the defects on the reticle is performed by the one or more computer subsystems.

Each of the steps of the method may be performed as described further herein. The method may also include any other step(s) that can be performed by the inspection subsystem and/or computer subsystem(s) or system(s) described herein. The steps of the method are performed by various components (e.g., the one or more image processing components, the main user interface component, and the interface component) of one or more computer subsystems as described further herein and which may be configured according to any of the embodiments described herein. In addition, the method described above may be performed by any of the system embodiments described herein.

Figure 10:
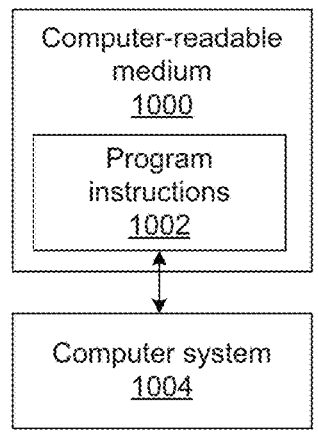
FIG. 10 is a block diagram illustrating one embodiment of a non-transitory computer-readable medium storing program instructions executed on a computer system for performing one or more of the computer-implemented methods described herein.

An additional embodiment relates to a non-transitory computer-readable medium storing program instructions executed on a computer system for performing a computer-implemented method for detecting defects on a reticle. One such embodiment is shown in FIG. 10. In particular, as shown in FIG. 10, non-transitory computer-readable medium 1000 includes program instructions 1002 executable on computer system 1004. The computer-implemented method may include any step(s) of any method(s) described herein.

Program instructions 1002 implementing methods such as those described herein may be stored on computer-readable medium 1000. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 1004 may be configured according to any of the embodiments described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another SW module, method, or system, etc. For example, the defects detected on the reticle may be used to control and/or alter a reticle repair or cleaning process in which the goal is to remove or repair one or more reticle defects to thereby prevent such reticle defects from being printed on other wafers. In one such example, information for the defects detected on the reticle may be used by the one or more computer subsystems described herein, another system (e.g., a reticle repair system), or another method a reticle repair method) to determine where on a reticle a reticle repair or cleaning process should he performed. The information for the defects detected on the reticle may also be used to determine one or more parameters of such a process such as the area on which the process is to be performed, the length of time that the process is to be performed, which chemicals or gases should be used in the process, etc. In this manner, the altered reticle can be used to print the dies on the reticle on other wafers in the lithography process. The altered reticle may also be re-inspected using the embodiments described herein at another time after it has been re-introduced to the lithography process.

Further modifications and alternative embodiments of various aspects of the invention will be apparent to those skilled in the art in view of this description. For example, systems and methods for detecting defects on a reticle are provided. Accordingly, this description is to be construed as illustrative only and for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a reticle, comprising:
    an inspection subsystem configured to scan a wafer to thereby generate images for the wafer, wherein a reticle is used to print features on the wafer in a lithography process; and
    one or more computer subsystems comprising:
        one or more image processing components configured for acquiring the images generated by the inspection subsystem for the wafer;
        a main user interface component configured for providing information generated for the wafer and the reticle to a user and for receiving instructions from the user; and
        an interface component configured for providing an interface between t one or more image processing components and the main user interface component and for controlling one or more hardware elements of the inspection subsystem;
        wherein the one or more image processing components are further configured for performing repeater defect detection by applying a repeater defect detection algorithm to the images acquired by the one or more image processing components, and wherein the repeater defect detection algorithm is configured to detect defects on the wafer using a hot threshold and to identify the defects that are repeater defects;
        wherein the one or more image processing components are further configured for sending inspection results comprising information for only the repeater defects to the interface component; and
        wherein the one or more computer subsystems are configured for identifying defects on the reticle based on the repeater defects detected on the wafer.

2. The system of claim 1, wherein the repeater defect detection algorithm is further configured to identify the defects that are the repeater defects by comparing the within die defect coordinates for different of the defects to each other.

3. The system of claim 1, wherein the one or more image processing components are further configured for storing information for all of the detected defects.

4. The system of claim 1, wherein performing the repeater defect detection is performed for only a single swath on the wafer.

5. The system of claim 1, wherein the one or more image processing components are further configured as a virtual inspector, and wherein the one or more computer subsystems are further configured for disconnecting the virtual inspector from the inspection subsystem after the images are acquired from the inspection subsystem and before the repeater defect detection is performed.

6. The system of claim 1, wherein the one or more image processing components are further configured for performing single swath-multiple die row defect detection by applying a defect detection algorithm to the images generated by the inspection subsystem for the same single swath in multiple die rows on the wafer and for sending results of the single swath-multiple die row defect detection to the interface component, and wherein the interface component or the main user interface component performs repeater defect detection on the results of the single swath-multiple die defect detection.

7. The system of claim I, wherein the one or more image processing components comprise a shared non-transitory computer-readable storage medium accessible for multiple processes performed by the one or more image processing components, and wherein the repeater defect detection algorithm is further configured to detect the defects on the entire inspected area of the wafer, to store all of the detected defects in the shared non-transitory computer-readable storage medium, and to identify the defects that are the repeater defects using all of the stored detected defects for the entire inspected area of the wafer.

8. The system of claim 1, wherein the one or more image processing components are further configured for performing single swath-multiple die row defect detection by applying a defect detection algorithm to the images generated by the inspection subsystem for the same single swath in multiple die rows on the wafer and storing results of the single swath-multiple die row defect detection in a shared non-transitory computer-readable storage medium in the one or more image processing components accessible for multiple processes performed by the one or more image processing components, and wherein the repeater defect detection algorithm is further configured to detect the defects in the entire inspected area of the same single swath in the multiple die rows, to store all of the detected defects in the shared non-transitory computer-readable storage medium, and to identify the defects that are the repeater defects using all of the stored detected defects for the entire inspected area of the same single swath in the multiple die rows.

9. The system of claim 1, wherein the one or more image processing components comprise a shared non-transitory computer-readable storage medium accessible for multiple processes performed by the one or more image processing components, wherein the one or more computer subsystems further comprise a virtual inspector, wherein the one or more image processing components are further configured for storing only a first portion of results produced by the repeater defect detection algorithm in the shared non-transitory computer-readable storage medium and only a second portion of the results produced by the repeater defect detection algorithm in the virtual inspector, wherein the first portion comprises only defect coordinates for the defects detected on the wafer, wherein the second portion comprises only defect attributes and patch images for the detected defects on the wafer, wherein the repeater defect detection algorithm is further configured to identify the repeater defects using only the first portion of the results, and wherein the one or more image processing components are further configured for retrieving the defect attributes and patch images for the repeater defects from the virtual inspector and generating the inspection results by combining information generated by identifying the repeater defects with the retrieved defect attributes and patch images.

10. The system of claim 1, wherein the one or more image processing components comprise a shared non-transitory computer-readable storage medium accessible for multiple processes performed by the one or more image processing components, wherein the one or more image processing components are further configured for storing only a first portion of results produced by the repeater defect detection algorithm in the shared non-transitory computer-readable storage medium, wherein the first portion comprises only defect coordinates for the defects detected on the wafer, Wherein the repeater defect detection algorithm is further configured to identify the repeater defects using only the first portion of the results, wherein the interface component is further configured for controlling the one or more hardware elements of the inspection subsystem to thereby scan only locations on the wafer of the identified repeater defects, and wherein the one or more image processing components are further configured for combining images generated in the scan of only the locations on the wafer of the identified repeater defects with the first portion of the results to thereby generate the inspection results that are sent to the interface component.

11. The system of claim 1, wherein the repeater defect detection algorithm is further configured to identify the defects that appear at the same location in two or more printed instances of the reticle on the wafer as the repeater defects.

12. The system of claim 1, wherein the one or more computer subsystems are further configured for identifying the defects on the reticle by determining which of the repeater defects repeat in two or more printed instances of the reticle on the wafer and identifying the repeater defects that repeat in the two or more printed instances of the reticle on the wafer as the defects on the reticle.

13. The system of claim 1, wherein identifying the defects on the reticle is performed by the main user interface component included in the one or more computer subsystems.

14. The system of claim 1, wherein the repeater defect detection algorithm is further configured to detect the defects by generating three or more difference images for each test frame of the images generated for the wafer by subtracting three or more reference frames from the test frame, respectively, applying at least one threshold to the three or more difference images, and determining that a defect is present in the test frame when results of two or more of said applying the at least one threshold to the three or more difference images indicate that a defect is present.

15. The system of claim 1, wherein the repeater defect detection algorithm is further configured to detect the defects by comparing each test frame of the images generated for the wafer to an average of multiple reference frames.

16. The system of claim 1, wherein the repeater defect detection algorithm is further configured to detect the detects by generating a mean of multiple frames of the images generated for the wafer corresponding to the same location within each reticle instance printed on the wafer and subtracting the mean from reference frames from dies on the wafer at different locations within multiple reticle instances printed on the wafer.

17. The system of claim 1, wherein the repeater defect detection algorithm is further configured to detect the defects by generating a mean of multiple frames of the images generated for the wafer corresponding to the same location within each reticle instance printed on the wafer and subtracting the mean from a mean of reference frames from other dies at different locations within multiple reticle instances printed on the wafer.

18. The system of claim 1, wherein the repeater defect detection algorithm is further configured to identify the defects that are the repeater defects by adding image frames corresponding to a location of a detected defect in multiple instances of the reticle printed on the wafer, comparing the added image frames to a threshold, and determining that the defect is a repeater defect when the added image frames are above the threshold.

19. The system of claim 1, wherein the repeater defect detection algorithm is further configured a) to detect the defects and to identify the defects that are the repeater defects in only a first swath by identifying the defects that appear at the same location in a first number of instances of the reticle printed on the wafer as the repeater defects and b) to subsequently detect the defects and to identify the defects that are the repeater defects in other swaths by identifying the defects that appear at the same location in a second number of instances of the reticle printed on the wafer as the repeater defects, and wherein the second number is higher than the first number.

20. The system of claim 19, wherein the repeater defect detection algorithm is further configured to reduce noise in the first swath by filtering out systematic noise that occurs in every instance of the reticle printed on the wafer in the first swath and at the same location in each die instance of the reticle printed on the wafer in the first swath.

21. The system of claim 1, wherein the repeater defect detection algorithm is further configured to detect the defects by comparing image frames of reticle instances printed on the wafer to a standard image frame generated from a different wafer.

22. The system of claim 1, wherein the repeater defect detection algorithm is further configured to detect the defects by comparing image frames of reticle instances printed on the wafer to a median image frame generated from a different wafer.

23. The system of claim 1, wherein the repeater defect detection algorithm is further configured to detect the defects by comparing image frames of reticle instances printed on the wafer to a rendered design.

24. The system of claim 1, wherein the hot threshold comprises a local multiple die adaptive threshold.

25. The system of claim 1, wherein the one or more image processing components are further configured for storing information for the detected defects in shared memory per node of the one or more image processing components.

26. The system of claim 25, wherein the information stored for the detected defects in the shared memory comprises information for only defects detected in one or more first die rows on the wafer.

27. The system of claim 26, wherein the repeater defect detection algorithm is further configured to identify the defects that are the repeater defects by identifying defects detected in adjacent dies in the one or more first die rows at the same die relative locations as the repeater defects and identifying defects not detected in the adjacent dies in the one or more first die rows at the same die relative locations as non-repeater defects.

28. The system of claim 27, wherein the repeater defect detection algorithm is further configured to identify the defects that are the repeater defects by identifying defects detected in adjacent dies in other die rows on the wafer at the same die relative locations as the repeater defects and identifying defects not detected in the adjacent dies in the other die rows at the same die relative locations as non-repeater defects.

29. The system of claim 28, wherein the repeater defect detection algorithm is further configured to identify the defects that are the repeater defects by extracting portions of the images generated for the wafer at the same die relative locations as the non-repeater defects and applying a local defect detection algorithm to the extracted portions of the images to thereby determine if undetected defects repeat at the same die relative locations as the non-repeater defects.

30. The system of claim 1, wherein the repeater defect detection algorithm is further configured to align the images generated for the wafer to a design for the wafer with sub-pixel accuracy.

31. The system of claim 1, wherein the repeater defect detection algorithm is further configured to determine which of the repeater defects are defects of interest and which of the repeater defects are nuisances using a machine learning technique performed based on attributes of the repeater defects, properties of the images corresponding to the repeater defects, or a combination thereof.

32. The system of claim 1, wherein the repeater defect detection algorithm is further configured to align the images generated for the wafer to each other by identifying a common alignment target in two portions of the images processed by the repeater defect detection algorithm as two different jobs, respectively, aligning the two different jobs to each other using the common alignment target, determining an alignment offset based on results of said aligning, and applying the alignment offset to other jobs to thereby align the other jobs to the two different jobs.

33. The system of claim 32, wherein the two different jobs are located in different die rows on the wafer.

34. A non-transitory computer-readable medium, storing program instructions executed on one or more computer subsystems for performing a computer-implemented method for detecting defects on a reticle, wherein the computer-implemented method comprises:
acquiring images generated for a wafer by an inspection subsystem, wherein a reticle is used to print features on the wafer in a lithography process, and wherein said acquiring is performed by one or more image processing components included in the one or more computer subsystems;
wherein the one or more computer subsystems comprise a main user interface configured for providing information generated for the wafer and the reticle to a user and for receiving instructions from the user; and
wherein the one or more computer subsystems further comprise an interface component configured for providing an interface between the one or more image processing components and the main user interface component and for controlling one or more hardware elements of the inspection subsystem;
performing repeater defect detection by applying a repeater defect detection algorithm to the images acquired by the one or more image processing components, wherein the repeater defect detection algorithm is configured to detect defects on the wafer using a hot threshold and to identify the defects that are repeater defects, and Wherein the repeater defect detection is performed by the one or more image processing components;
sending inspection results comprising information for only the repeater defects from the one or more image processing components to the interface component; and
identifying defects on the reticle based on the repeater defects detected on the wafer, wherein identifying the defects on the reticle is performed by the one or more computer subsystems.

35. A computer-implemented method for detecting defects on a reticle, comprising:
acquiring images generated for a wafer by an inspection subsystem, wherein a reticle is used to print features on the wafer in a lithography process, and
wherein said acquiring is performed by one or more image processing components included in one or more computer subsystems;
wherein the one or more computer subsystems comprise a main user interface configured for providing information generated for the wafer and the reticle to a user and for receiving instructions from the user; and
wherein the one or more computer subsystems further comprise an interface component configured for providing an interface between the one or more image processing components and the main user interface component and for controlling one or more hardware elements of the inspection subsystem;
performing repeater defect detection by applying a repeater defect detection algorithm to the images acquired by the one or more image processing components, wherein the repeater defect detection algorithm is configured to detect defects on the wafer using a hot threshold and to identify the defects that are repeater defects, and wherein the repeater defect detection is performed by the one or more image processing components;
sending inspection results comprising information for only the repeater defects from the one or more image processing components to the interface component; and
identifying defects on the reticle based on the repeater defects detected on the wafer, wherein identifying the defects on the reticle is performed by the one or more computer subsystems.

* * * * *

UNITED STATES PATENT AND TRADEMARK OFFICE
CERTIFICATE OF CORRECTION

PATENT NO. : 10,395,358 B2
APPLICATION NO. : 15/804980
DATED : August 27, 2019
INVENTOR(S) : Bjorn Brauer et al.

Page 1 of 1

It is certified that error appears in the above-identified patent and that said Letters Patent is hereby corrected as shown below:

In the Claims

Column 35
Line 47, please delete "t" and substitute --the--.

Column 36
Line 28, please delete "l" and substitute --1--.

Column 37
Line 25, please delete "Wherein" and substitute --wherein--.

Column 38
Line 2, please delete "detects" and substitute --defects--.

Column 40
Line 16, please delete "Wherein" and substitute --wherein--.

Signed and Sealed this
Tenth Day of December, 2019

Andrei Iancu
*Director of the United States Patent and Trademark Office*